United States Patent [19]

Bushell et al.

[11] Patent Number: 4,791,139
[45] Date of Patent: Dec. 13, 1988

[54] DIPHENYL ETHER DERIVATIVES AND THEIR USE AS INSECTICIDES

[75] Inventors: Michael J. Bushell, Wokingham; Robin A. E. Carr, Camberley, both of England

[73] Assignee: Imperial Chemical Industries PLC, London, England

[21] Appl. No.: 18,712

[22] Filed: Feb. 25, 1987

[30] Foreign Application Priority Data

Mar. 4, 1986 [GB] United Kingdom ............... 8605281

[51] Int. Cl.$^4$ ................ A16K 31/335; A16K 31/44; A16K 31/03; A16K 31/045; A16K 31/08; A16K 31/085; A16K 3/09; C07F 9/28; C07F 9/02; C07C 43/03; C07C 43/205; C07D 213/26

[52] U.S. Cl. .................... 514/721; 514/89; 514/100; 514/129; 514/141; 514/277; 514/338; 514/345; 514/351; 514/357; 514/449; 514/450; 514/452; 514/465; 514/475; 514/646; 514/657; 514/719; 514/720; 514/726; 514/744; 514/745; 514/746; 514/749; 570/127; 570/128; 570/129; 546/22; 546/24; 546/303; 546/330; 546/339; 546/344; 546/345; 558/388; 558/401; 558/402; 558/410; 549/362; 549/434; 568/11; 568/14; 568/15; 568/631; 568/634; 568/635; 568/637; 568/639; 568/640; 568/641; 568/645; 568/647; 568/807; 568/808; 568/809; 568/812

[58] Field of Search .......... 546/303, 22, 24, 330, 546/339, 344, 345; 570/127, 128, 129; 568/11, 14, 15, 647, 644, 655, 656, 807, 808, 809, 812; 558/388, 410, 401, 402; 549/434, 362; 514/338, 277, 345, 351, 357, 450, 452, 449, 465, 475, 89, 100, 129, 141, 646, 726, 749, 746, 719, 720, 744, 721, 745, 651

[56] References Cited

U.S. PATENT DOCUMENTS 4,678,811 7/1987 Franke et al. .................. 514/721

FOREIGN PATENT DOCUMENTS 0104908 4/1984 European Pat. Off. .......... 546/22
0191723 7/1984 European Pat. Off. .......... 546/312
0233834 8/1987 European Pat. Off. .......... 568/11
2120664 7/1983 United Kingdom ............. 546/22

Primary Examiner—Mary C. Lee
Assistant Examiner—J. Richter
Attorney, Agent, or Firm—Cushman, Darby & Cushman

[57] ABSTRACT

A compound of formula:

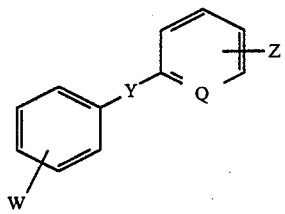

wherein W represents one or more substituents selected from halo, alkyl, alkoxy, alkoxyalkyl, haloalkyl and haloalkoxy or W represents a bidentate group linking adjacent carbon atoms selected from alkylene and alkylenedioxy; Y is a group of formula

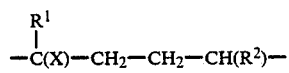

or

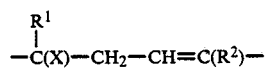

or

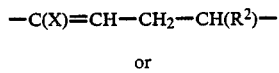

or

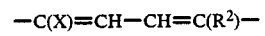

wherein X is a group of formula —(CF$_2$)$_n$R$^3$, where R$^3$ is selected from hydrogen, chloro and fluoro, and n is one or two, R$^1$ is selected from hydrogen, chloro, fluoro and hydroxy and R$^2$ is selected from methyl, cyano, ethynyl and hydrogen; Q is selected from carbon bearing a hydrogen atom and nitrogen; and Z represents one or more substituents selected from fluoro, benzyl, phenoxy, chlorophenoxy, fluorophenoxy and bromophenoxy, or any isomer thereof. Processes for preparing these compounds and intermediates for use therein, insecticidal compositions containing these compounds and the use thereof are also disclosed.

9 Claims, No Drawings

DIPHENYL ETHER DERIVATIVES AND THEIR USE AS INSECTICIDES

This invention relates to novel fluorinated aralkyl derivatives having useful insecticidal properties, to processes for preparing them, to intermediates for use in such processes and to insecticidal compositions and methods of combating pests therewith.

The invention provides chemical compounds of the general formula (I):

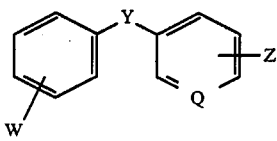

(I)

wherein W represents one or more substituents selected from halo, alkyl, alkoxy, alkoxyalkyl, haloalkyl and haloalkoxy or W represents a bidentate group linking adjacent carbon atoms selected from alkylene and alkylenedioxy; Y is a group of formula

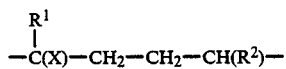

or

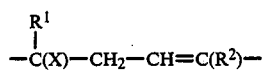

or

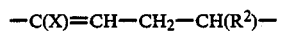

or

wherein X is a group of formula $-(CF_2)_nR^3$, where $R^3$ is selected from hydrogen, chloro and fluoro, and n is one or two, $R^1$ is selected from hydrogen, chloro, fluoro and hydroxy and $R^2$ is selected from methyl, cyano, ethynyl and hydrogen; Q is selected from carbon bearing a hydrogen atom and nitrogen; and Z represents one or more substituents selected from fluoro, benzyl, phenoxy, chlorophenoxy, fluoropheoxy and bromopheoxy.

Preferred compounds according to the invention are those according to formula (II):

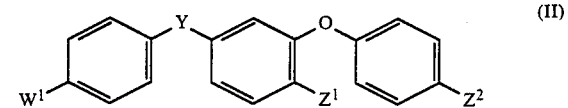

(II)

wherein Y has any of the meanings hereinbefore described; $W^1$ is selected from halo, alkyl of up to six carbon atoms, alkoxy of up to six carbon atoms, haloalkyl of up to six carbon atoms and haloalkoxy of up to six carbon atoms; $Z^1$ is selected from hydrogen and fluoro and $Z^2$ is selected from hydrogen and halo.

Particularly preferred compounds according to the invention are those according to formula (III):

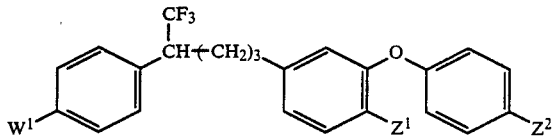

wherein $W^1$ is an alkoxy group of up to two carbon atoms or a fluoroalkoxy group of up to two carbon atoms, for example methoxy, ethoxy, trifluoromethoxy or difluoromethoxy, or a fluoroalkyl group of up to two carbon atoms, for example trifluoromethyl or difluoromethyl; $Z^1$ is selected from hydrogen and fluoro and $Z^2$ is selected from hydrogen and halo.

Particular examples of compounds according to the invention include those set out in Table I below. All of the compounds in Table I correspond to formula I given hereinbefore. For convenience, the group shown as

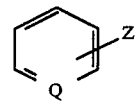

in formula I is represented in Table I by $E^1-E^{10}$ wherein $E^1$ to $E^{10}$ have the following meanings:

$E^1$: 3-phenoxyphenyl
$E^2$: 3-(4-chlorophenoxy)phenyl
$E^3$: 4-fluoro-3-phenoxyphenyl
$E^4$: 3-(4-fluorophenoxy)phenyl
$E^5$: 4-fluoro-3-(4-chlorophenoxy)phenyl
$E^6$: 4-fluoro-3-(4-bromopheoxy)phenyl
$E^7$: pentafluorophenyl
$E^8$: 6-phenoxypyrid-2-yl
$E^9$: 3-benzylphenyl
$E^{10}$: 4-fluoro-3-benzylphenyl

TABLE I

| Compound No. | W | Y | Q | Isomer Composition (E:Z) |
|---|---|---|---|---|
| 1 | 4-OC$_2$H$_5$ | $-C(CF_3)=CH-(CH_2)_2-$ | $E^1$ | 4:1 |
| 2 | 4-OC$_2$H$_5$ | $-CH(CF_3)-(CH_2)_3-$ | $E^1$ | |
| 3 | 4-OC$_2$H$_5$ | $-C(CF_3)=CH-(CH_2)_2-$ | $E^1$ | E |
| 4 | 4-OC$_2$H$_5$ | $-C(CF_3)=CH-(CH_2)_2-$ | $E^1$ | Z |
| 5 | 4-OC$_2$H$_5$ | $-CH(CF_3)-(CH_2)_3-$ | $E^3$ | |
| 6 | 4-C(CH$_3$)$_3$ | $-C(CF_3)=CH-(CH_2)_2-$ | $E^1$ | 7:2 |
| 7 | 4-OCF$_3$ | $-C(CF_3)=CH-(CH_2)_2-$ | $E^1$ | 1:1 |
| 8 | 4-C(CH$_3$)$_3$ | $-CH(CF_3)-(CH_2)_3-$ | $E^1$ | |
| 9 | 4-OCF$_3$ | $-CH(CF_3)-(CH_2)_3-$ | $E^1$ | |
| 10 | 4-OC$_2$H$_5$ | $-C(C_2F_5)=CH-(CH_2)_2-$ | $E^1$ | 33:5 |
| 11 | 4-OC$_2$H$_5$ | $-CH(C_2F_5)-(CH_2)_3-$ | $E^1$ | |
| 12 | 4-OC$_2$H$_5$ | $-C(CF_3)=CH-CH=CH-$ | $E^3$ | (2E, 4E): |

TABLE I-continued

| Compound No. | W | Y | Q 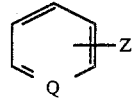 -Z | Isomer Composition (E:Z) |
|---|---|---|---|---|
| | | | | (2E, 4Z) 1:1 |
| 13 | 4-Cl | —CH(CF$_3$)—(CH$_2$)$_3$— | E$^2$ | |
| 14 | 4-OC$_2$H$_5$ | —CH(CF$_3$)—(CH$_2$)$_3$— | E$^4$ | |
| 15 | 4-CF$_3$ | —C(CF$_3$)=CH—(CH$_2$)$_2$— | E$^1$ | 2:3 |
| 16 | 4-CF$_3$ | —CH(CF$_3$)—(CH$_2$)$_3$— | E$^1$ | |
| 17 | 4-CF$_3$ | —C(CF$_3$)=CH—(CH$_2$)$_2$— | E$^3$ | |
| 18 | 4-CF$_3$ | —CH(CF$_3$)—(CH$_2$)$_3$— | E$^3$ | |
| 19 | 4-OCF$_3$ | —C(CF$_3$)=CH—(CH$_2$)— | E$^3$ | 1:1 |
| 20 | 4-OCF$_3$ | —CH(CF$_3$)—(CH$_2$)$_3$— | E$^3$ | |
| 21 | 4-OC$_2$H$_5$ | —C(CF$_3$)=CH—(CH$_2$)$_2$— | E$^3$ | |
| 22 | 4-CF$_3$ | —C(CF$_3$)=CH—(CH$_2$)$_2$— | E$^5$ | |
| 23 | 4-CF$_3$ | —CH(CF$_3$)—(CH$_2$)$_3$— | E$^5$ | |
| 24 | 4-OC$_2$H$_5$ | —C(CF$_3$)=CH—(CH$_2$)$_2$— | E$^6$ | |
| 25 | 4-OC$_2$H$_5$ | —CH(CF$_3$)—(CH$_2$)$_3$— | E$^6$ | |
| 26 | 4-OCF$_3$ | —C(CHF$_2$)=CH—(CH$_2$)$_2$— | E$^3$ | 10:1 |
| 27 | 4-OCF$_3$ | —C(CHF$_2$)—(CH$_2$)$_3$— | E$^3$ | |
| 28 | 4-CF$_3$ | —C(CF$_2$Cl)=CH—(CH$_2$)$_2$— | E$^1$ | |
| 29 | 4-CF$_3$ | —CH(CF$_2$Cl)—(CH$_2$)$_3$— | E$^1$ | |
| 30 | 4-OCF$_3$ | —C(CF$_3$)=CH—CH=CH— | E$^3$ | (2E, 4E): (2Z, 4E) 85:15 |
| 31 | 4-OC$_2$H$_5$ | —CH(CF$_3$)—CH$_2$—CH=CH— | E$^1$ | 6:4 |
| 32 | 4-OC$_2$H$_5$ | —CH(CF$_3$)—CH$_2$—CH=CH— | E$^3$ | 6:4 |
| 33 | 4-Cl | —C(CF$_3$)=CH—(CH$_2$)$_2$— | E$^1$ | 55:45 |
| 34 | 4-OC$_2$H$_5$ | —CH(CF$_3$)—CH$_2$—CH=CH— | E$^1$ | E |
| 35 | 4-OC$_2$H$_5$ | —CH(CF$_3$)—CH$_2$—CH=CH— | E$^1$ | Z |
| 36 | 4-OC$_2$H$_5$ | —C(CF$_3$)=CH—CH=CH— | E$^3$ | (2E, 4E) |
| 37 | 4-OC$_2$H$_5$ | —C(CF$_3$)=CH—CH=CH— | E$^3$ | (2E, 4Z) |
| 38 | 4-Cl | —CH(CF$_3$)—(CH$_2$)$_3$— | E$^1$ | |
| 39 | 4-Br | —C(CF$_3$)=CH—(CH$_2$)$_3$— | E$^1$ | 1:1 |
| 40 | 3,4-(OCH$_2$O) | —CH(CF$_3$)—(CH$_2$)$_3$— | E$^1$ | |
| 41 | 3,4-(OCH$_2$O) | —C(CF$_3$)=CH—(CH$_2$)$_2$— | E$^1$ | 1:2 |
| 41 | 4-OC$_2$H$_5$ | —CH(CF$_3$)—CH$_2$—CH=CH— | E$^7$ | 2:1 |
| 43 | 4-OC$_2$H$_5$ | —CH(CF$_3$)—(CH$_2$)$_3$— | E$^7$ | |
| 44 | 4-CH$_2$OCH$_3$ | —C(CF$_3$)=CH—(CH$_2$)$_2$— | E$^1$ | 7:3 |
| 45 | 4-CH$_2$OCH$_3$ | —CH(CF$_3$)—(CH$_2$)$_3$— | E$^1$ | |
| 46 | 4-OCH$_3$ | —C(CF$_3$)=CH—(CH$_2$)$_2$— | E$^1$ | 4:1 |
| 47 | 4-F | —C(CF$_3$)=CH—(CH$_2$)$_2$— | E$^1$ | 55:45 |
| 48 | 3,4-(CH$_2$)$_3$ | —C(CF$_3$)=CH—(CH$_2$)$_2$— | E$^1$ | 3:1 |
| 49 | 4-OCH$_3$ | —CH(CF$_3$)—(CH$_2$)$_3$— | E$^1$ | |
| 50 | 3-F, 4-OC$_2$H$_5$ | —C(CF$_3$)=CH—(CH$_2$)$_2$— | E$^1$ | 5:3 |
| 51 | 3,5-F$_2$, 4-OC$_2$H$_5$ | —C(CF$_3$)=CH—(CH$_2$)$_2$— | E$^1$ | 4:5 |
| 52 | 3,4-(CH$_2$)$_3$ | —CH(CF$_3$)—(CH$_2$)$_3$— | E$^1$ | |
| 53 | 4-F | —CH(CF$_3$)—(CH$_2$)$_3$— | E$^1$ | |
| 54 | 4-OC$_2$H$_5$ | —CH(CF$_3$)—(CH$_2$)$_2$—CH(CN)— | E$^1$ | |
| 55 | 4-OC$_2$H$_5$ | —CH(CF$_3$)—(CH$_2$)$_2$—CH(CH$_3$)— | E$^1$ | |
| 56 | 3-F, 4-OC$_2$H$_5$ | —CH(CF$_3$)—(CH$_2$)$_3$— | E$^1$ | |
| 57 | 3,5-F$_2$, 4-OC$_2$H$_5$ | —CH(CF$_3$)—(CH$_2$)$_3$— | E$^1$ | |
| 58 | 3,4-(OC(CH$_3$)$_2$O) | —CH(CF$_3$)—(CH$_2$)$_3$— | E$^1$ | |
| 59 | 4-OCF$_3$ | —C(OH)(CF$_3$)—(CH$_2$)$_3$— | E$^1$ | |
| 60 | 4-OCF$_3$ | —C(F)(CF$_3$)—(CH$_2$)$_3$— | E$^1$ | |
| 61 | 3,4-(OCH(CH$_3$)O) | —CH(CF$_3$)—(CH$_2$)$_3$— | E$^1$ | |
| 62 | 4-OCF$_3$ | —C(Cl)(CF$_3$)—(CH$_2$)$_3$— | E$^1$ | |
| 63 | 4-OCF$_2$CF$_2$H | —CH(CF$_3$)—(CH$_2$)$_3$— | E$^1$ | |
| 64 | 3,5-F$_2$, 4-OC$_2$H$_5$ | —CH(CF$_3$)—(CH$_2$)$_3$— | E$^3$ | |
| 65 | 4-OC$_2$H$_5$ | —C(CHF$_2$)=CH—CH=CH— | E$^1$ | (2E, 4E): (2Z, 4E) 3:1 |
| 66 | 4-OC$_2$H$_5$ | —CH(CHF$_2$)—(CH$_2$)$_3$— | E$^1$ | |
| 67 | 3,5-F$_2$, 4-OC$_2$H$_5$ | —C(CF$_3$)=CH—CH=CH— | E$^3$ | (2E, 4E): (2Z, 4E) 5:1 |
| 68 | 4-OCF$_2$CF$_2$Br | —CH(CF$_3$)—(CH$_2$)$_3$— | E$^1$ | |
| 69 | 4-OC$_2$H$_5$ | —CH(CF$_2$Cl)—(CH$_2$)$_3$— | E$^1$ | |
| 70 | 4-OCF$_3$ | —C(CF$_2$Cl)=CH—CH=CH— | E$^1$ | (2E, 4E): (2Z, 4E) 13:1 |
| 71 | 3,5-F$_2$, 4-OCF$_3$ | —CH(CF$_3$)—(CH$_2$)$_3$— | E$^1$ | |
| 72 | 2,4-F$_2$, 3-OCF$_3$ | —CH(CF$_3$)—(CH$_2$)$_3$— | E$^1$ | |
| 73 | 4-OCH$_2$CF$_3$ | —CH(CF$_3$)—(CH$_2$)$_3$— | E$^1$ | |
| 74 | 2-Br, 5-OCF$_3$, 4,6-F$_2$ | —C(CF$_3$)=CH—CH=CH— | E$^1$ | (2E, 4E): (2Z, 4E) 1:1 |
| 75 | 3,5-F$_2$, 4-OCF$_3$ | —C(CF$_3$)=CH—CH=CH— | E$^1$ | |
| 76 | 4-OCF$_3$ | —C(CF$_2$Cl)=CH—CH=CH— | E$^3$ | (2E, 4E): (2Z, 4E) |

TABLE I-continued

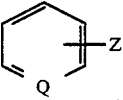

| Compound No. | W | Y | Q | Isomer Composition (E:Z) |
|---|---|---|---|---|
| 77 | 4-OCF₃ | —C(CF₂H)=CH—CH=CH— | E³ | 12:1 (2E, 4E): (2Z, 4E) 9:1 |
| 78 | 4-OC₂H₅ | —C(Cl)(CF₃)—(CH₂)₃— | E¹ | |
| 79 | 4-OC₂H₅ | —C(F)(CF₃)—(CH₂)₃— | E¹ | |
| 80 | 4-OC₂H₅ | —C(OH)(CF₃)—(CH₂)₃— | E¹ | |
| 81 | 4-OCF₃ | —C(CF₃)=CH—CH=CH— | E¹ | (2E, 4E): (2Z, 4E) 6:1 |
| 82 | 4-OCF₃ | —C(CHF₂)=CH—CH=CH— | E¹ | (2E, 4E): (2Z, 4E) 5:1 |
| 83 | 4-OCF₃ | —CH(CHF₂)—(CH₂)₃— | E¹ | |
| 84 | 4-OCF₃ | —CH(CF₂Cl)—(CH₂)₃— | E³ | |
| 85 | 4-OC₂H₅ | —CH(CHF₂)—(CH₂)₃— | E³ | |
| 86 | 4-OC₂H₅ | —C(CHF₂)=CH—CH=CH— | E³ | |
| 87 | 4-Cl | —CH(CHF₂)—(CH₂)₃— | E³ | |
| 88 | 4-Cl | —CH(CF₃)—(CH₂)₃— | E³ | |
| 89 | 4-OCF₃ | —CH(CF₃)—(CH₂)—CH(CN)— | E¹ | |
| 90 | 4-OCF₃ | —CH(CF₃)—(CH₂)₂—CH(CH₃)— | E¹ | |
| 91 | 4-OC₂H₅ | —CH(CF₃)—(CH₂)₃— | E² | |
| 92 | 4-OCF₃ | —CH(CF₃)—(CH₂)₃— | E² | |
| 93 | 4-OC₂H₅ | —CH(CF₃)—(CH₂)₃— | E⁵ | |
| 94 | 4-OCF₃ | —CH(CF₃)—(CH₂)₃— | E⁵ | |
| 95 | 4-OCF₃ | —C(CF₃)=CH—CH=CH— | E⁸ | |
| 96 | 4-OCF₃ | —CH(CF₃)—CH₂—CH=CH— | E⁸ | |
| 97 | 4-OCF₃ | —CH(CF₃)—(CH₂)₃— | E⁸ | |
| 98 | 4-OC₂H₅ | —CH(CF₃)—(CH₂)₃— | E⁸ | |
| 99 | 4-OC₂H₅ | —CH(CF₃)—CH₂—CH=CH— | E⁸ | 3:1 |
| 100 | 4-OC₂H₅ | —C(CF₃)=CH—CH=CH— | E⁸ | |
| 101 | 4-OCHF₂ | —CH(CF₃)—(CH₂)₃— | E¹ | |
| 102 | 4-OCHF₂ | —CH(CF₃)—(CH₂)₃— | E³ | |
| 103 | 4:OCF₃ | —C(CF₃)=CH—CH=CH— | E⁹ | |
| 104 | 4-OC₂H₅ | —CH(CF₃)—(CH₂)₃— | E⁹ | |
| 105 | 4-OCF₃ | —C(CF₃)=CH—CH=CH— | E¹⁰ | (2E, 4E): (2Z, 4E) 86:14 |
| 106 | 4-OC₂H₅ | —CH(CF₃)—(CH₂)₃— | E¹⁰ | |
| 107 | 4-OC₂H₅ | —C(CF₃)=CH—CH=CH— | E¹⁰ | (2E, 4E): (2Z, 4E) 86:14 |
| 108 | 4-OCF₃ | —CH(CF₃)—(CH₂)₃— | E¹⁰ | |
| 109 | 4-OCF₃ | —CH(CF₃)—(CH₂)₃— | E⁹ | |
| 110 | 4-OC₂H₅ | —C(CF₃)=CH—CH=CH— | E⁹ | |
| 111 | 3,4-(OCH(CH₃)O) | —C(CF₃)=CH—(CH₂)₂— | E¹ | 3:7 |
| 112 | 3,4-(OC(CH₃)₂O) | —C(CF₃)=CH—(CH₂)₂— | E¹ | 3:1 |
| 113 | 4-OC₂H₅ | —C(CF₂Cl)=CH—CH=CH— | E¹ | (2E, 4E): (2Z, 4E) 4:1 |
| 114 | 4-OCF₃ | —C(CF₃)=CH—CH=CH— | E³ | (2Z, 4E) |
| 115 | 4-OCF₃ | —C(CF₃)=CH—CH=CH— | E³ | (2E, 4E): (2Z, 4E) 1:1 |
| 116 | 4-OC₂H₅ | —CH(CF₃)—CH₂—CH=C(CN)— | E¹ | |
| 117 | 4-OC₂H₅ | —CH(CF₃)—CH₂—CH=C(CH₃)— | E¹ | |
| 118 | 4-CH₃ | —C(CF₃)=CH—CH=CH— | E¹ | |
| 119 | 4-CH₃ | —C(CF₃)=CH—CH=CH— | E³ | |
| 120 | 4-CH₃ | —CH(CF₃)—(CH₂)₃— | E¹ | |
| 121 | 4-CH₃ | —CH(CF₃)—(CH₂)₃— | E³ | |
| 122 | 4-(CH₂)₂CH₃ | —C(CF₃)=CH—CH=CH— | E¹ | |
| 123 | 4-(CH₂)₂CH₃ | —CH(CF₃)—(CH₂)₃— | E¹ | |
| 124 | 4-(CH₂)₂CH₃ | —C(CF₃)=CH—CH=CH— | E³ | |
| 125 | 4-(CH₂)₂CH₃ | —CH(CF₃)—(CH₂)₃— | E³ | |

Those compounds of the invention for which the linking group Y in formula I contains one or two carbon-carbon double bonds may exhibit geometric isomerism, with each double bond able to exist in either the E or the Z form. Where the group Y contains one such double bond, the individual isomers may be depicted in the following way:

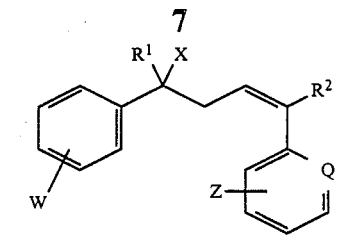

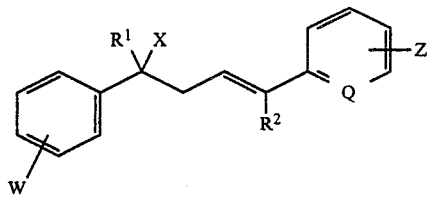

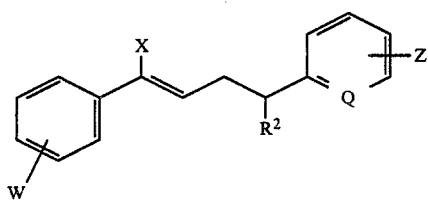

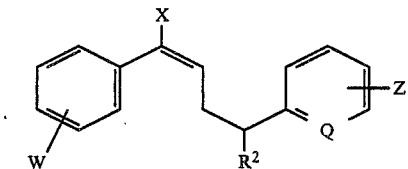

Where the group Y contains two such double bonds, the individual isomers may be depicted in the following way:

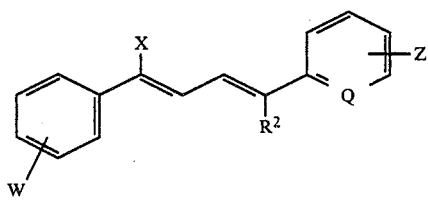

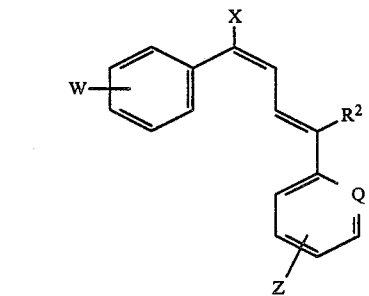

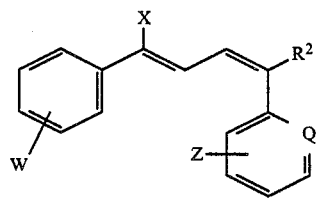

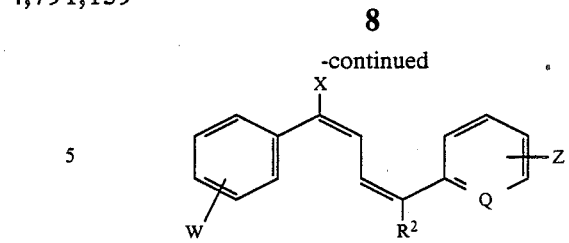

-continued

Those compounds of the invention containing one or more asymmetrically substituted carbon atoms can exist in alternative enantiomeric or diastereoisomeric forms.

Different isomeric forms of the invention compounds may exhibit different insecticidal properties and it is believed that most of the insecticidal activity of an invention compound may be associated with one individual isomer or group of isomers. It is to be understood that all individual isomeric forms and mixtures, including racemic mixtures, of such isomeric forms are included within the scope of the invention.

The geometric isomer composition for those compounds in Table I containing double bonds is given, where appropriate and where known, in terms of the ratio of E:Z isomers for each double bond in the linking group Y.

Where compounds in Table I contain asymmetrically substituted carbon atoms, they are present in racemic form.

The compounds of the invention may fall into a number of structural types according to the values of Y, $R^1$ and $R^2$; a number of these structural types are illustrated below:

IA

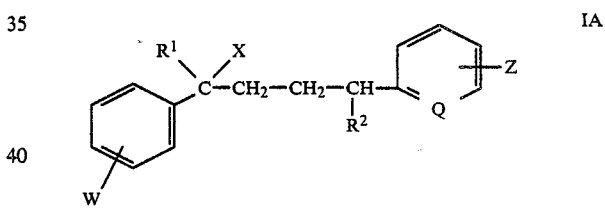

IB

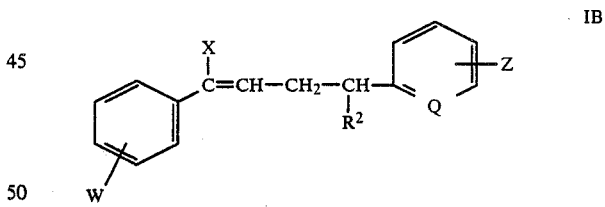

IC

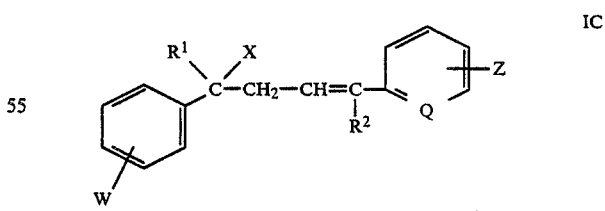

ID

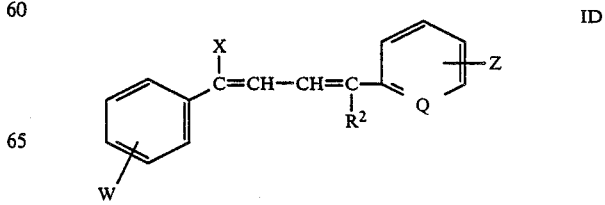

The compounds of formula IA wherein $R^1$ is hydrogen may be prepared by reduction of the corresponding compounds of formula IB, IC and ID using a process of catalytic hydrogenation. A suitable hydrogenation catalyst is palladium supported on charcoal, with from 5 to 20% by weight of palladium present. The hydrogenation is conveniently carried out by passing hydrogen gas under a pressure of from 1.5 to 20 atmospheres of hydrogen, preferably from 2 to 5 atmospheres, into a solution of the compound of formula IB, IC or ID in a suitable solvent such as a lower alkanol, eg. methanol or ethanol. The compounds of formula IA wherein both $R^1$ and $R^2$ are hydrogen may also be prepared from the corresponding compound of formula IA wherein $R^1$ is chlorine by reduction using for example tri-n-butyl tin hydride as reducing agent.

The compounds of formula IB wherein $R^2$ is hydrogen may be prepared from a corresponding compound of formula IV:

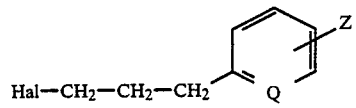

(IV)

wherein Hal represents chloro, bromo or iodo, by a Wittig reaction, such as that illustrated in Scheme A. An example of a procedure suitable for the preparation of a compound of formula (IV) is summarised in Scheme B.

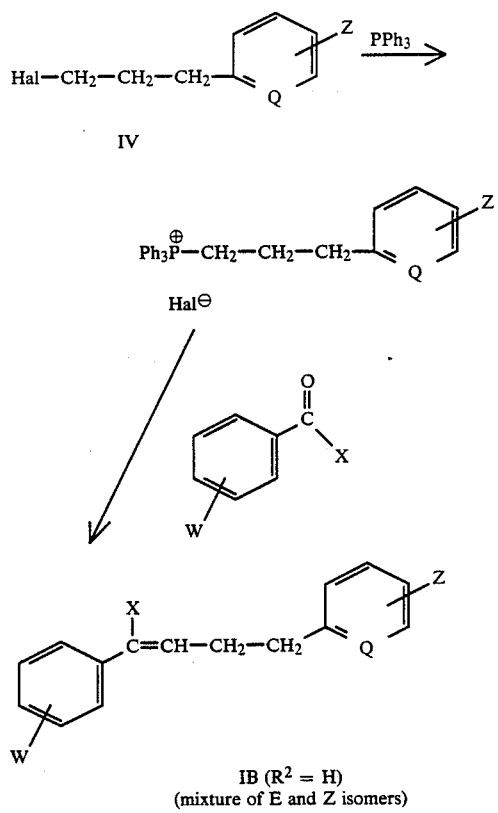

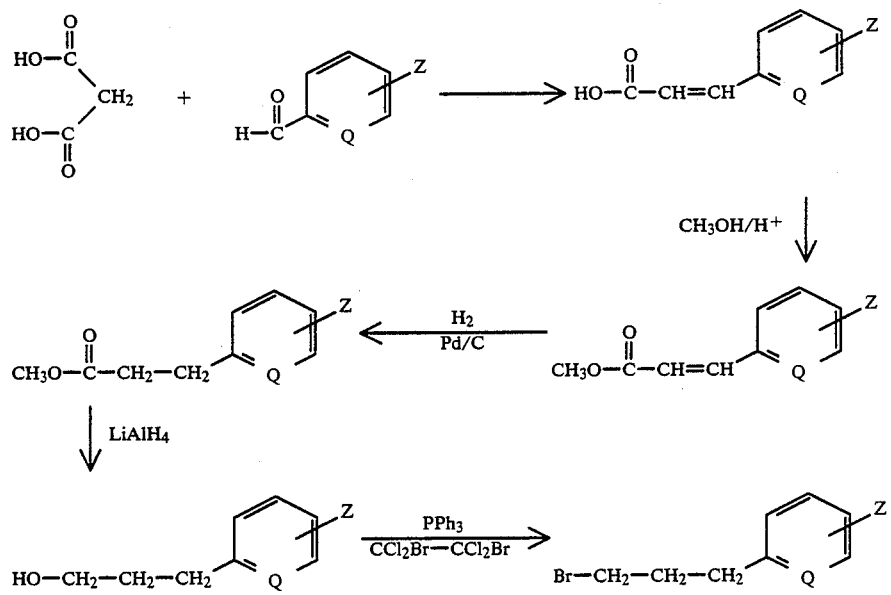

The compounds of formula IC may be prepared from alkyl haloacetates and the appropriate aryl ketone by a procedure analogous to that illustrated in Scheme C.

Scheme C
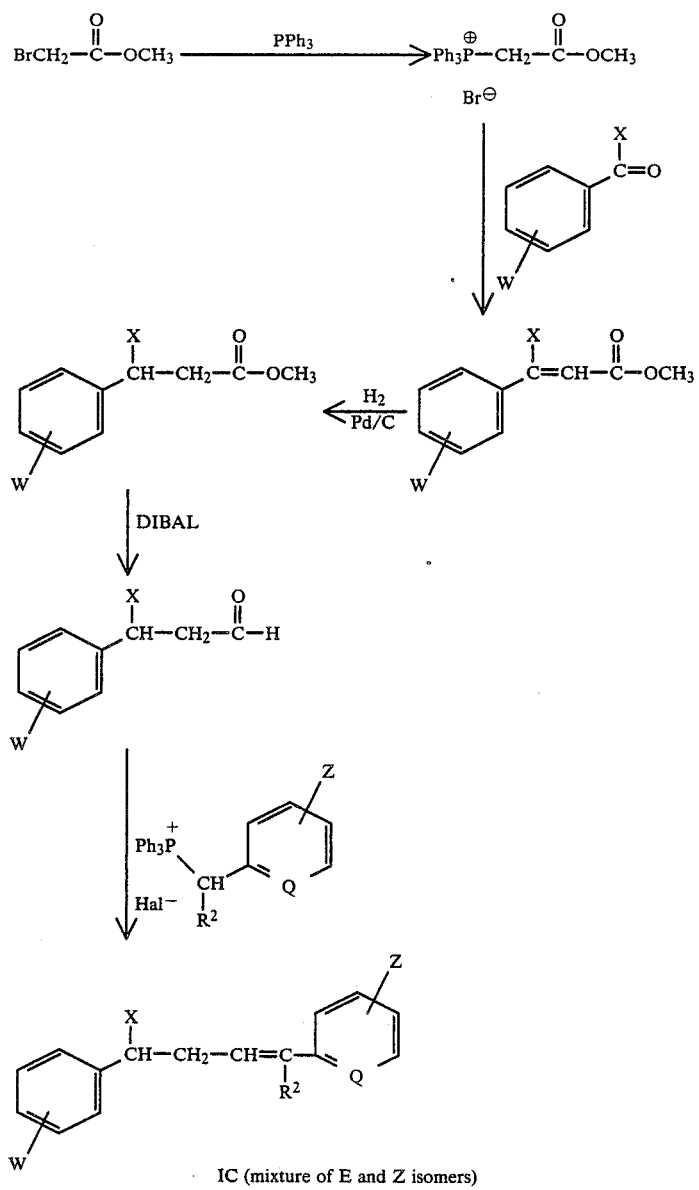
IC (mixture of E and Z isomers)
The compounds of formula ID may be prepared by processes analogous to those summarised in Schemes D and E.
Scheme D
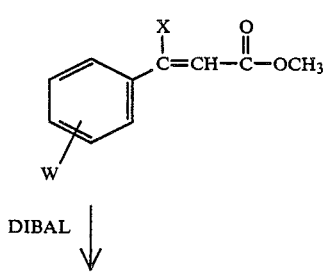
DIBAL ↓
-continued
Scheme D
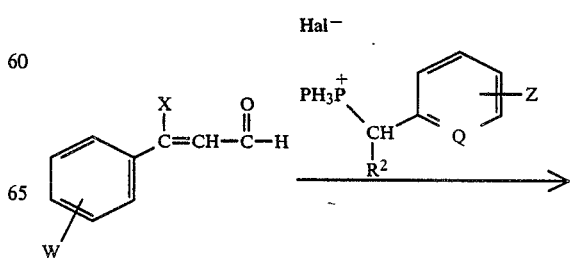

13

-continued
Scheme D

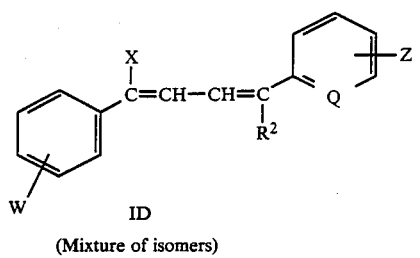

ID
(Mixture of isomers)

Any of the Wittig alkene syntheses described in Schemes A to E may be performed using phosphonates as an alternative to the phosphonium salts illustrated in the schemes. The phosphonates may be prepared by reaction of the appropriate halo compound with a phosphite, for example trimethyl phosphite. Formation of the required alkene may then be achieved by reaction of the phosphonate with the appropriate ketone or aldehyde in the presence of a strong base, for example n-butyllithium.

The compounds of formula IA wherein $R^2$ is hydrogen and $R^1$ is hydroxy, chloro or fluoro may be prepared by processes analogous to those summarised in Scheme F.

Scheme E

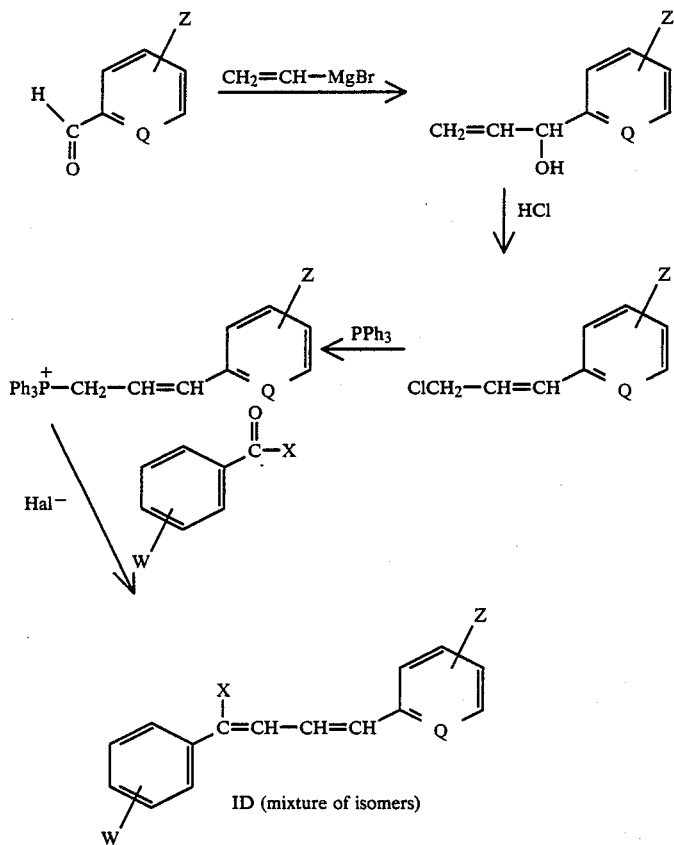

ID (mixture of isomers)

Scheme F

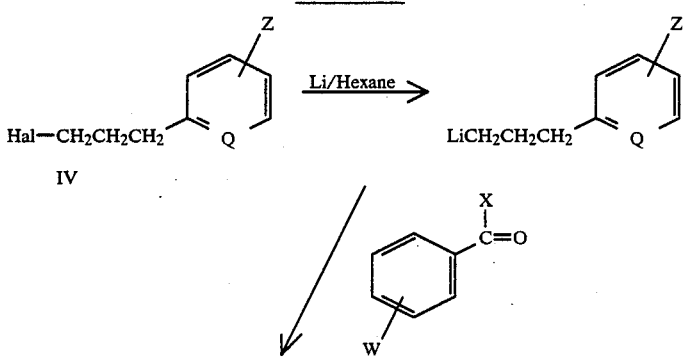

Scheme F

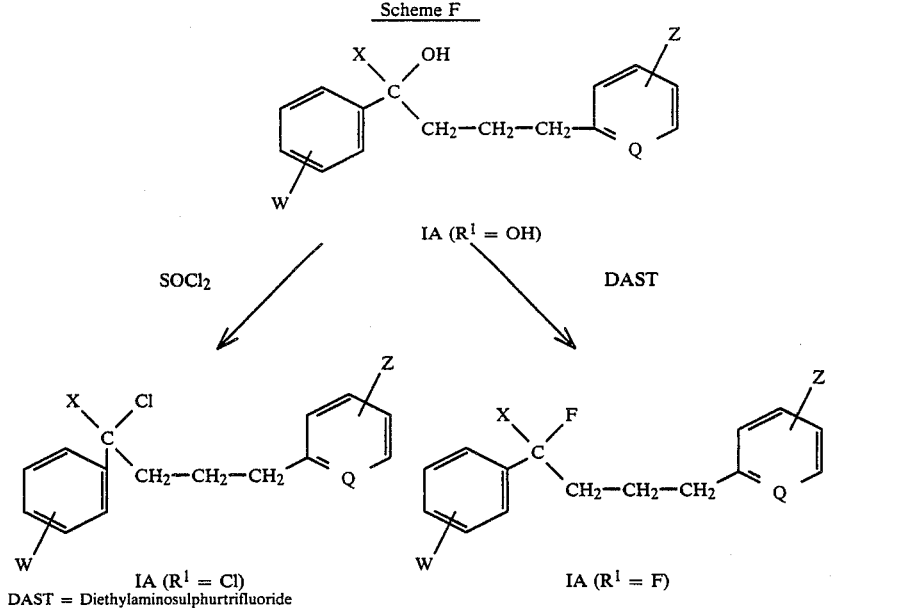

IA ($R^1$ = OH)

DAST = Diethylaminosulphurtrifluoride

The compounds of formula

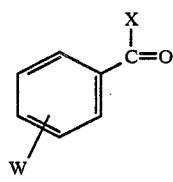

widely used in the Schemes illustrated hereinbefore, may be prepared by the methods illustrated in Scheme G.

Scheme G

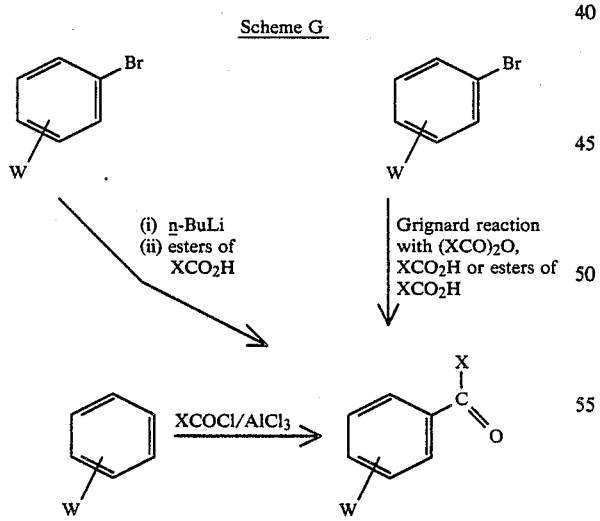

These procedures are analogous to those illustrated in UK Patent Application No. 2178739 for the preparation of trifluoroacetophenone derivatives.

Compounds of formula I wherein W represents a 4-haloalkoxy substituent may be prepared by an alternative route by reaction of a 4-hydroxy compound of formula VI with a haloalkyl bromide or a haloalkyldiazonium salt. Compounds of formula I wherein W represents a fluoroalkoxy substituent may also be prepared by reaction of a compound of formula VI with the appropriate perfluorinated alkene.

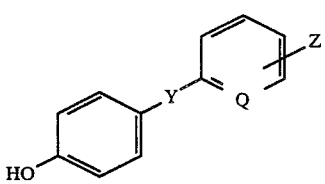

Compounds of formula VI may themselves be prepared by dealkylation of the corresponding compound wherein W represents lower alkoxy, for example methoxy, by the action of a standard dealkylating agent, for example pyridinium hydrochloride or boron tribromide.

Certain intermediates described in Scheme B are believed to be novel. Accordingly, in a further aspect, the invention provides compounds of formula

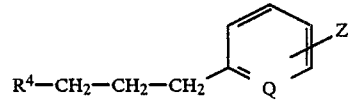

wherein Q and Z have any of the meanings given hereinbefore and $R^4$ is selected from hydroxy, bromo, chloro and iodo, or $R^4$ is selected from a group of formula

and a group of formula

wherein R represents alkyl or aryl, for example

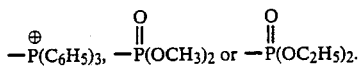

Compounds of formula I wherein X is CF$_2$H may be prepared by the methods described hereinbefore or may alternatively be prepared by the selective reduction of the corresponding compounds wherein X is CF$_2$Cl, for example using tri-n-butyl tin hydride as the selective reducing agent.

Compounds according to formula I having one or more asymmetric centre are normally prepared in the form of mixtures of the stereoisomers concerned. These mixtures may be separated, for example by chromatographic means using a chiral fixed phase, such as the Pirkle type IA column. Compounds of formula IA produced by reduction of compounds of formula IB, IC or ID may be produced in a form containing an excess of one stereoisomer by the use of a chiral catalytic reducing agent.

Separation of geometric isomers of invention compounds containing one or more carbon-carbon double bonds within the linking group Y may also be achieved by chromatographic means, for example high pressure liquid chromatography.

Further details of the above-mentioned processes are set out in the Examples hereinafter.

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds of the locus of the pests they are usually formulated into compositions which include in addition to the insecticidally active ingredient or ingredients of formula I suitable insert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of his type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenmethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones such as juvenile hormone juvabione, or ecdysones.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluzuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 5–95% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula I and compositions comprising them are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitos)
Anopheles spp. (mosquitos)
*Culex* spp. (mosquitos)
Dysdercus fasciatus (capsids)
Musca domestica (houseflies)
*Pieris brassicae* (white butterfly, larvae)
*Plutella maculipennis* (diamond back moth, larvae)
Phaedon cochleariae (mustard beetle)
*Tetranychus cinnabarinus* (carmine spider mite)
*Tetranychus urticae* (red spider mites)
*Aonidiella* spp. (scale insects)
*Trialeuroides* spp. (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
*Chilo Partellus* (maize stem borers)
*Nilaparvata lugens* (plant hoppers)
*Nephotettix cinticeps* (plant hoppers)

The compounds according to formula I and compositions comprising them have shown themselves to be particularly useful in controlling pests of maize and rice such as Chilo (stem borers), Nilaparvata and Nephotettix (plant hoppers) as well as lepidopteran pests of cotton, for example Heliothis spp. This activity is combined with a low level of hazard to aquatic organisms, eg. fish, which renders the compounds particularly suitable for use in aquatic environments, such as for the control of insect pests of paddy rice and for the control of larvae of insect vectors of disease, for example mosquitos. Thus, for example, compound 2 in Table I caused no mortality to carp after 48 hours at a concentration of 10 parts per million. The compounds according to formula I have also exhibited particularly useful levels of acaricidal activity, for example against Tetranychus spp. (spider mites).

The following Examples illustrate various aspects of this invention. In the preparation Examples the products were usually identified and characterised by means of nuclear magnetic reasonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chromopak, C.P. Sil 5 C.B. column of 12.5M length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

¹H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz ¹H NMR spectrometry were performed using Jeol FX 90Q, Jeol PMX 60SI and Jeol GX400 spectrometers respectively.

¹⁹F NMR spectrometry was performed on a Jeol FX90Q spectrometer at a frequency of 84.26 MHz. All NMR shift values are quoted in ppm relative to a standard (TMS or CFCl$_3$).

Molecular Ion (M+) peaks were determined on one of three mass spectrometers: Jeol DX303, Kratos MS80 or Hewlett Packard HP 5992.

EXAMPLE 1

This Example illustrates the preparation of 4-bromo-α,α,α-trifluoroacetophenone.

Literature reference: Journal of Organometallic Chemistry, 251, 139–148, (1983).

A mixture of 1,4-dibromobenzene (64 g), dry tetrahydrofuran (600 cm$^3$) and dry diethyl ether (600 cm$^3$) was cooled to −78° C. under an atmosphere of nitrogen. n-Butyllithium (108.4 cm$^3$ of a 2.5 molar solution in hexane) was added to the stirred mixture over 40 minutes, the temperature of the reaction mixture being maintained below −72° C. by external cooling; the mixture was then stirred for a further 40 minutes. Methyl trifluoroacetate (35.4 g) was then added over 40 minutes, and stirring continued for a further 30 minutes, the temperature being maintained below −68° C. throughout. The reaction mixture was then carefully quenched by adding a mixture of concentrated hydrochloric acid (60 cm$^3$) and ethanol (40 cm$^3$), precooled to −78° C., over a period of 10 minutes. After stirring for a further 20 minutes, the reaction mixture was allowed to warm to the ambient temperature (ca. 22° C.). The organic layer was separated and concentrated by evaporation under reduced pressure to leave a water-contaminated oil (70 g). The oil was dissolved in diethyl ether, and the solution dried over anhydrous magnesium sulphate. Evaporation of the solvent under reduced pressure gave an orange oil, which was purified by distillation under reduced pressure (ca. 15 mm Hg). Two fractions containing essentially the same material, 4-bromo-α,α,α-trifluoroacetophenone, were obtained. The first fraction (17.19 g), boiling within a range of 78°–83° C., was shown to be 85% pure by gas liquid chromatography; the second fraction (41.13 g), boiling range 83°–84° C., was shown to be 99% pure by gas liquid chromatography. The second fraction crystallised on standing.

¹H NMR (CDCl$_3$) δ(ppm): 7.7 (2H, m); 7.95 (2H, m)
¹⁹F NMR (CDCl$_3$) δ(ppm—relative to CFCl$_3$): −72.1

EXAMPLE 2

By the use of a procedure similar to that illustrated in Example 1 above, the following compounds were prepared from the appropriate starting materials.

(i) 3-Fluoro-4-ethoxy-α,α,α-trifluoroacetophenone, from 4-bromo-2-fluorophenetole.

The preparation of 4-bromo-2-fluorophenetole is described in Example 41.

In this case, the product was purified by column chromatography on a silica gel support, eluting with n-hexane containing 5% by volume ethyl acetate.

¹H NMR (CDCl$_3$) δ(ppm): 1.54 (3H, t); 4.2 (2H, q); 7.0 (1H, t); 7.7–7.95 (2H, m).

(ii) 4-Methoxymethyl-α,α,α-trifluoroacetophenone, from 4-bromobenzyl methyl ether.

The preparation of 4-bromobenzylmethyl ether is described in Example 40.

¹H NMR (CDCl$_3$) δ(ppm): 3.45 (3H, s); 4.57 (2H, s); 7.5, 8.05 (4H, ABq)

IR (liquid film): 1722 cm$^{-1}$ (C=O)

GLC retention time: 1.67 minutes.

(iii) 3,4-(Methylenedioxy)-α,α,α-trifluoroacetophenone, from 4-bromo-1,2-(methylenedioxy)benzene.

¹H NMR (CDCl$_3$) δ(ppm): 6.12 (2H, s); ca. 6.9 (1H, d); 7.5 (1H, broad, s); ca. 7.7 (1H, broad d)

GLC retention time: 1.87 minutes (iv) 4-Trifluoromethoxy-α,α,α-trifluoroacetophenone, from 4-bromotrifluoromethoxybenzene.

4-Bromotrifluoromethoxybenzene may be prepared from trifluoromethoxybenzene by the process described in the Journal of Organic Chemistry, 29, 1, (1964).

Boiling point: 164°–166° C. (atmosphere pressure).

¹H NMR (CDCl$_3$) δ(ppm): 7.35, 8.14 (4H, d)

¹⁹F NMR (CDCl$_3$) δ(ppm relative to CFCl$_3$): −58.1 (s) CF$_3$O −72.1 (s) CF$_3$ GLC retention time: 1.50 minutes (50° C.–280° C. run)

(v) 3,4-(Dimethylmethylenedioxy)-α,α,α-trifluoroacetophenone, from 4-bromo-1,2-(dimethylmethylenedioxy)benzene ¹H NMR (CDCl$_3$) δ(ppm): 1.72 (6H, s); 6.84 (1H, d); 7.43 (1H, broad s); 7.65 (1H, broad d)

infra red (liquid film): 1708 cm$^{-1}$

The preparation of 4-bromo-1,2-(dimethylmethylenedioxy)benzene is described in Example 38.

(vi) 3,4-(Methylmethylenedioxy)-α,α,α-trifluoroacetophenone from 4-bromo-1,2-(methylmethylenedixoy)benzene ¹H NMR (CDCl$_3$) δ(ppm): 1.74 (3H, d); 6.42 (1H, q); 6.86 (1H, d); 7.45 (1H, broad s); 7.7 (1H, broad d)

Infra red (liquid film): 1712 cm$^{-1}$

The preparation of 4-bromo-1,2-(methylmethylenedioxy)benzene is described in Example 39.

(vii) 4-Trifluoromethoxy-α,α-difluoro-α-chloroacetophenone from 4-bromotrifluoromethoxybenzene and methyl chlorodifluoroacetate.

¹H NMR (CDCl$_3$) δ(ppm): ca 7.4 (2H, m); 8.2 (2H, m)

¹⁹F NMR (CDCl$_3$) δ(ppm—relative to CFCl$_3$): −58.1 (CF$_3$O, s); −61.61 (CF$_2$Cl, S).

EXAMPLE 3

This Example illustrates the preparation of 4-ethoxy-α,α,α-trifluoroacetophenone.

A. From trifluoroacetic acid.

Literature reference: Journal of Organic Chemsitry, 32, 1311, (1967).

A solution of 4-bromo-ethoxybenzene (60 g) in diethyl ether (100 cm$^3$) was added slowly to a stirred mixture of magnesium turnings (7.4 g), diethyl ether (50 cm$^3$) and iodine (ca. 0.5 g) under a nitrogen atmosphere. After ca. 15 cm$^3$ of the solution had been added the mixture was warmed gently until the reaction commenced and the rate of addition was thereafter adjusted to maintain a gentle reflux. After the completion of the addition (ca. 30 minutes) the mixture was stirred for a further 20 minutes at the ambient temperature (ca. 22° C.), following which a solution of trifluoroacetic acid (12.0 g) in diethyl ether (25 cm$^3$) was added dropwise over a period of one hour. The mixture was then heated at the reflux temperature for a further one hour after which the mixture was poured into crushed ice and acidified with concentrated hydrochloric acid. The organic layer was separated, and the aqueous layer extracted three times with diethyl ether and the extracts combined with the organic layer, and the ethereal solution washed twice with saturated sodium bicarbonate, and dried over anhydrous sodium sulphate. After removal of the solvent by evaporation under reduced pressure the residual oil (48 g) was subjected to fractional distillation. Three fractions were collected at 64° C./0.1–0.2 mg Hg, containing 1.2 g (75% pure by gas-liquid chromatography), 13 g (91% pure) and 2.4 g (85% pure) of 4-ethoxytrifluoroacetophenone respectively. The major fraction was used without further purification.

$^1$H NMR (CDCl$_3$) δ: 1.46 (3H, t); 4.15 (2H, q); 7.0 (2H, m); 8.05 (2H, m).

Infra red (liquid film): 1710 cm$^{-1}$.

B. From trifluoroacetic anhydride.

A solution of 4-bromoethoxybenzene (150 g) in diethyl ether (200 cm$^3$) was added slowly to a stirred mixture of magnesium turnings (20.0 g), diethyl ether (50 cm$^3$) and iodine (ca. 0.5 g) under a nitrogen atmosphere. After ca. 35 cm$^3$ of the solution had been added the mixture was warmed gently until the reaction commenced and the rate of addition was adjusted to maintain a gentle reflux. After the addition was complete the mixture was stirred for a further one hour at the ambient temperature (ca. 22° C.) after which the mixture was cooled to 0° C. by external cooling and a solution of trifluoroacetic anhydride (203 g) in diethyl ether (100 cm$^3$) was added, initially drop by drop, and then at a faster rate so as to maintain a gentle reflux. The addition was completed over a period of 20 minutes after which the mixture was stirred for a further 45 minutes. The mixture was then poured onto crushed ice and the product worked up in the manner set out in Part A above, to give, after distillation, 4-ethoxytrifluoroacetophenone (35 g).

EXAMPLE 4

By the use of procedures similar to those set out in parts A and B of Example 3 above, the following compounds were prepared from the appropriate starting material.

(i) 4-Methoxy-α,α,α-trifluoroacetophenone, from 4-bromomethoxybenzene and trifluoroacetic anhydride.

$^1$H NMR (CDCl$_3$) δ(ppm): 3.90 (3H, s); 7.02 (2H, d); 8.05 (2H, d)

GLC retention time: 3.75 minutes (50° C.–280° C. run)

(ii) 4-t-Butyl-α,α,α-trifluoroacetophenone, from 4-bromo-t-butylbenzene and trifluoroacetic anhydride.

GLC retention time: 1.83 minutes (iii) 4-Trifluoromethoxy-α,α,α-trifluoroacetophenone, from 4-bromotrifluoromethoxybenzene and trifluoroacetic anhydride.

In this case, the product was purified by distillation in a Kugelrohr apparatus, under reduced pressure (ca. 12 mm Hg), at an oven temperature of 50°–70° C.

$^1$H NMR (CDCl$_3$) δ(ppm): 7.35, 8.14 (4H, d)

$^{19}$F NMR (CDCl$_3$) δ: (ppm-relative to CFCl$_3$): −58.1 (CF$_3$O, S) −72.1 (CF$_3$, S)

IR: 1730, 1610, 1270, 1150–1250 cm$^{-1}$ (iv) 4-Chloro-α,α,α-trifluoroacetophenone, from 4-bromochlorobenzene and trifluoroacetic anhydride.

$^1$H NMR (CDCl$_3$) δ(ppm): ca. 7.6, 8.1 (each 2H, ABq)

GLC retention time: 2.56 minute (50° C.–280° C. run)

EXAMPLE 5

This Example illustrates the preparation of 4-ethoxy-α,α-difluoro-α-chloroacetophenone.

Magnesium turnings (2.64 g), diethyl ether (dried over molecular sieves, 50 cm$^3$) and a few crystals of iodine were placed in a 3 neck round-bottom flask and were stirred under an atmosphere of nitrogen. About 10% of a solution of 4-bromo phenetole (20 g) in dry diethyl ether (100 cm$^3$) was added, and the mixture was warmed gently to initiate the Grignard reaction. When the reaction had begun, the rest of the bromophenetole solution was added at a rate sufficient to maintain a gentle reflux. At the end of the addition the solution was stirred for one hour.

Methyldifluorochloroacetate (28.75 g) in diethylether (100 cm$^3$) was placed in a flask under nitrogen and cooled to about −7° C. (internal temperature). The solution of the 4-ethoxyphenyl magnesium bromide was added dropwise with stirring, then the mixture was allowed to warm to the ambient temperature for about half an hour. The mixture was quenched with water and acidified with hydrochloric acid to assist solubilisation of the magnesium salts. The layers were separated and the aqueous phase was extracted twice with diethylether. The combined ether layers were washed twice with water, then dried over anhydrous magnesium sulphate before being concentrated by evaporation under reduced pressure to give a golden brown oil (22.7 g). The oil was heated at about 110° C. under reduced pressure (ca. 15 mmHg) to remove residual phenetole. The residual oil was then distilled under high vacuum (ca. 0.1 mmHg). A forefraction boiling between 60° C. and 80° C. was discarded, and the product was distilled at about 80° C., and was shown to be 97% pure by gas liquid chromatography (3.24 g).

$^1$H NMR (CDCl$_3$) δ(ppm): 1.46 (3H, t); 4.16 (2H, q); ca. 7.0 and 8.1 (each 2H, d)

$^{19}$F NMR (CDCl$_3$) δ(ppm—relative to CFCl$_3$): −60.7 (CF$_2$, Cl, s); infra (liquid film): 1710 cm$^{-1}$

EXAMPLE 6

This Example illustrates the stages in the preparation of 3,5-difluoro-4-ethoxy-α,α,α-trifluoroacetophenone.

Stage 1—preparation of 4-bromo-2,6-difluorophenol.

A solution of bromine (1.6 g) in dry carbon disulphide (10 cm$^3$) was added over 5 minutes to a solution of 2,6-difluorophenol (1.3 g) in dry carbon disulphide (10 cm$^3$). To the stirred reaction mixture was added 5 drops of 48% hydrogen bromide solution. The mixture was heated for 2 hours at the reflux temperature, then allowed to stand at the ambient temperature (ca 22° C.) for 16 hours. After a further period of heating (4 hours) the mixture was allowed to stand for 24 hours before being poured onto water (20 cm$^3$). To the mixture was added saturated sodium metabisulphite solution (30 cm$^3$). The layers were separated, and the organic phase was washed with saturated sodium hydrogen carbonate solution (20 cm$^3$) and water (20 cm$^3$). The organic layer was dried over anhydrous sodium sulphate then evaporated under reduced pressure to given an oil which solidified. The crude product was distilled in a Kugelrohr apparatus at an oven temperature of 100° C. under reduced pressure (ca. 20 mmHg). The distillate crystallised to give 4-bromo-2,6-difluorophenol as a white solid (0.48 g).

¹H NMR (CDCl₃) δ(ppm): ca 7.1 (2H, d); ca 5.1 (1H, broad)

Stage 2—Preparation of 4-bromo-2,6-difluorophenetole.

A solution of 4-bromo-2,6-difluorophenol (1.04 g) in dry N,N-dimethylformamide (10 cm³) was added over 5 minutes to a well stirred mixture of sodium hydride (0.24 g of a 50% dispersion in oil) in dry N,N-dimethylformamide (5 cm³).

After 30 minutes, ethyl iodide (0.78 g) was added in one portion. After stirring the reaction mixture for 30 minutes, analysis by gas liquid chromatography apparently showed no reaction; further ethyl iodide (5 g) was heated at 80° C. for 15 minutes. Later analysis showed similar retention times for both starting material and product, and the reaction may already have been complete prior to the second addition of ethyl iodide. The reaction mixture was poured into water, and extracted with ethyl acetate. The combined organic extracts were dried over anhydrous sodium sulphate and evaporated under reduced pressure to give a red oil. The oil was purified by column chromatography on a silica gel support, eluting with an 8:1 parts by volume mixture of n-hexane and ethyl acetate to give 4-bromo-2,6-difluorophenetole as a colourless oil (1.02 g).

¹H NMR (CDCl₃) δ(ppm): 1.45 (3H, t); 4.18 (2H, q); 7.06 (2H, m)

Stage 3—Preparation of 3,5-difluoro-4-ethoxy-α,α,α-trifluoroacetophenone

A solution of 4-bromo-2,6-difluorophenetole (17.5 g) in dry tetrahydrofuran (45 cm³) was added slowly to a stirred mixture of magnesium turnings (1.79 g) in dry tetrahydrofuran (50 cm³) containing a crystal of iodine under an atmosphere of nitrogen. The Grignard solution was transferred to a dropping funnel and was added over 4 minutes to a solution of freshly distilled trifluoroacetic anhydride (31 g) in dry diethyl ether (70 cm³) under an atmosphere of nitrogen; the reaction mixture was cooled in an ice bath during the addition. After 5 minutes the mixture was poured into ice, and stirred for 30 minutes. The products were extracted into diethyl ether and the organic phase was washed with water and sodium bicarbonate solution then dried over anhydrous sodium sulphate and the solvent evaporated under reduced pressure.

The residual oil was purified by chromatography on a silica gel support, eluting with n-hexane containing 10% by volume ethyl acetate, to give a yellow oil (10 g). This oil was distilled under reduced pressure (ca. 20 mmHg) using a Kugelrohr apparatus to give 3,5-difluoro-4-ethoxy-α,α,α-trifluoroacetophenone as a colourless oil (6.5 g).

¹H, NMR (CDCl₃) δ(ppm); 1.44 (3H, t); 4.44 (2H, m); ca 7.6 (2H m)

¹⁹F NMR (CDCl₃) δ(ppm—relative to CFCl₃) −71.9 (CF₃), −125.9 (2F, d)

EXAMPLE 7

This Example illustrates the stages in the preparation of 3,5-difluoro-4-trifluoromethoxy-α,α,α-trifluoroacetophenone and 2,4-difluoro-6-bromo-3-trifluoromethoxy-α,α,α-trifluoroacetophenone.

Stage 1

4-Bromo-2,6-difluorophenol was treated under pressure in an autoclave with hydrogen fluoride and carbon tetrachloride under conditions similar to those described for the preparation of 2-fluoro-4-bromotrifluoromethoxybenzene in European Patent Application No. 194064A. The residue was distilled at atmospheric pressure to remove dark material. Analysis of the distillate by gas chromatography-mass spectrometry showed the major product to be the expected 4-bromo-2,6-difluorotrifluoromethoxybenzene (Product A) and the minor component to be 4-bromo-2,6-difluoro(chlorodifluoromethoxy)benzene (Product B).

Further distillation gave the major product (Product A) in 92% purity (6.64 g) boiling at 144°–146° C. (atmospheric pressure).

Stage 2

4-Bromo-2,6-difluorotrifluoromethoxybenzene was reacted with n-butyl lithium and methyl trifluoroacetate according to the procedure described in Example 1. Competing ring lithiation gave rise to a second, unexpected product, identified as 2,4-difluoro-6-bromo-3-trifluoromethoxy-α,α-α-trifluoroacetophenone (Product B) in addition to the expected 3,5-difluoro-4-trifluoromethoxy-α,α,α-trifluoroacetophenone (Product A) in a ratio of 2:1. Separation of the ketones was not possible by distillation, and a 1:1 mixture of the two products resulting from distillation at atmospheric pressure was used without further isolation in a subsequent Wittig reaction.

Analysis by gas chromatography-mass spectrometry:
Product A: Molecular ion at 294
Product B: Molecular ion at 372/374

EXAMPLE 8

This Example illustrates the preparation of 4-ethoxy-α,α-difluoroacetophenone.

4-Ethoxy-α,α-difluoro-α-chloroacetophenone (1 g, prepared according to the method of Example 5), tri-n-butyl tin hydride (1.45 g), and a catalytic amount of α,α'-azobis-isobutyronitrile were mixed in dry toluene, maintained at 0° C. under a nitrogen atmosphere. The mixture was allowed to warm to room temperature and then heated at the reflux temperature for 4 hours. Analysis of a withdrawn portion of the reaction mixture showed some remaining starting ketone, so further tri-n-butyl tin hydride was added and heating continued for a further 30 minutes. The mixture was cooled, poured into water and separated. The aqueous layer was washed twice with ethyl acetate and the combined organic layers were dried over anhydrous magnesium sulphate, and the solvents evaporated under reduced pressure to give a pale yellow oil (2.9 g). The oil was distilled in a Kugelrohr apparatus and the major product-containing fraction was purified by chromatography on a silica gel support, eluting firstly with n-hexane containing 6% by volume ethyl acetate and secondly with ethyl acetate. 4-Ethoxy-α,α-difluoroacetophenone (0.3 g) was obtained as a yellow oil.

¹H NMR (CDCl₃) δ(ppm): 1.46 (3H, t); 4.14 (2H, q); 6.25 (1H, t, J=54 Hz); 6.97 and 8.06 (each 2H, d).

Molecular ion: 200

EXAMPLE 9

This Example illustrates the preparation of 4-ethoxypentafluoropropiophenone.

A solution of 4-bromo-ethoxybenzene (50 g) in dry diethyl ether (80 cm³) was added portionwise to a stirred mixture of magnesium turnings (6.0 g) and diethyl ether (20 cm³) to which a crystal of iodine (ca. 500 mg) had been added, maintained under a nitrogen atmosphere at the ambient temperature. After the reaction had commenced the rate of addition was adjusted to maintain gentle refluxing of the solvent. When the addition was complete the mixture was cooled to the ambient temperature and the stirring discontinued to allow any suspended solid particles to settle out. The supernatant solution of the Grignard reagent was then added dropwise to a stirred solution of pentafluoropropionic anhydride (100 g) in dry diethyl ether which had been pre-cooled to 0° C., and stirring was continued for a further 15 minutes. The mixture was poured into water, acidified with 2N hydrochloric acid, and extracted with four aliquots of diethyl ether. The combined extracts were dried over anhydrous sodium sulphate and concentrated by evaporation of the solvent under reduced pressure. The residual oil was subjected to careful distillation and the fraction boiling at 80°–90° C. at 0.5 mm Hg collected to yield 4-ethoxy-pentafluoropropiophenone (10 g) as a pale yellow oil which crystallised on standing and was recrystallised from hexane.

melting point 38°–39° C.

$^1$H NMR (CDCl$_3$) δ(ppm): 1.45 (3H, t); 4.22 (2H, q); 6.96 (2H, d); 7.06 (2H, d).

$^{19}$F NMR (CDCl$_3$) δ(ppm—relative to CFCl$_3$): −82.14 (CF$_3$); −115.68 (CF$_2$)

EXAMPLE 10

This Example illustrates the stages in the preparation of 3-(3-phenoxyphenyl)propyl triphenyl phosphonium bromide.

Stage 1: Preparation of E-3-(3-phenoxyphenyl)-propenoic acid

A mixture of 3-phenoxybenzaldehyde (214 g), malonic acid (300 g) and pyridine (450 cm$^3$) was heated at 50° C. until all the malonic acid had dissolved, after which piperidine (20 cm$^3$) was added and the mixture heated at 100° C. for 3 hours. The mixture was poured into iced water (3.0 l) and acidified with concentrated hydrochloric acid (600 cm$^3$). The precipitated solid was collected by filtration, washed with water and then dissolved in chloroform. The chloroform solution was washed with saturated sodium chloride solution and dried over anhydrous magnesium sulphate, after which the solvent was removed by evaporation under reduced pressure to give a solid residue which was recrystallised from a chloroform-hexane mixture to give E-3-(3-phenoxyphenyl)propenoic acid (219 g) as a white solid.

$^1$H NMR (CDCl$_3$) δ: 6.38 (d, J=18 Hz, 1H); 7.72 (d, J=18 Hz, 1H); 7.0–7.5 (m, 9H)

Stage 2: Preparation of methyl E-3-(3-phenoxyphenyl)-propenoate.

A mixture of E-3-(3-phenoxyphenyl)propenoic acid (210 g), methanol (1.0 l) and concentrated sulphuric acid (25 cm$^3$) was heated at the reflux temperature for 4 hours, after which the mixture was concentrated by evaporation of the methanol under reduced pressure until the volume was reduced to about 300 cm$^3$. After neutralising the acid present with aqueous potassium carbonate solution the mixture was diluted with water, extracted with chloroform and the chloroform extracts dried over anhydrous sodium sulphate. The chloroform was then removed by evaporation under reduced pressure to yield a residual oil (205 g) identified as methyl E-3-(3-phenoxyphenyl)propenoate.

$^1$H NMR (CDCl$_3$) δ: 3.78 (s, 3H); 6.36, 7.63 (2d, 1H); 7.0–7.4 (m, 9H)

Stage 3: Preparation of methyl 3-(3-(3-phenoxyphenyl)-propanoate

An atmosphere of hydrogen gas at a pressure of 60 psi was maintained for 3 hours over a stirred solution of E-3-(3-phenoxyphenyl)propanoate (79 g) in methanol (250 cm$^3$) in the presence of a hydrogenation catalyst (10% palladium on charcoal, 2.5 g) in a glass-lined steel pressure vessel. At the end of this period the catalyst was removed by filtration and the solution concentrated by evaporation of the methanol. The residual oil was purified by elution through a short silica gel column eluted with an ethyl acetate-hexane mixture, to yield methyl 3-(3-phenoxyphenyl)propanoate (70 g, 99.8% pure by gas-liquid chromatography).

$^1$H NMR (CDCl$_3$) δ: 2.5–3.05 (m, 4H); 3.66 (s, 3H); 6.8–7.4 (m, 9H)

Infra red (liquid film): 1745, 1592, 1490, 1255, 1220, 1170, 700 cm$^{-1}$

Stage 4: Preparation of 3-(3-phenoxyphenyl)propan-1-ol.

Lithium aluminium hydride (60 cm$^3$ of a 1M solution in tetrahydrofuran) was added dropwise over a period of 10 minutes to a stirred solution of methyl 3-(3-phenoxyphenyl)propanoate (25.6 g) in tetrahydrofuran (30 cm$^3$) whilst the temperature was maintained at 0° C. by external cooling. Stirring was continued for a further 45 minutes after which the mixture was allowed to warm up to the ambient temperature (ca. 22° C.). Iced water was added carefully to the mixture which was then acidified with dilute hydrochloric acid at pH2. The mixture was diluted with saturated sodium chloride solution and extracted with diethyl ether (×4) and with ethyl acetate. The combined extracts were dried over anhydrous sodium sulphate and concentrated by evaporation of the solvent under reduced pressure to yield 3-(3-phenoxyphenyl)propan-1-ol (22 g, 100% by gas-liquid chromatography) as a colourless oil.

$^1$H NMR (CDCl$_3$) δ: 1.5 (s, 1H); 1.6–2.05 (m, 2H); 2.5–2.85 (m, 2H); 3.63 (t, 2H); 6.7–7.5 (m, 9H).

Infra red (liquid film): 3360, 1588, 1486, 1445, 1250, 1220 cm$^{-1}$

Stage 5: Preparation of 3-(3-bromopropyl)diphenyl ether.

A solution of triphenylphosphine (13.0 g) in diethyl ether (50 cm$^3$) was added dropwise over a period of 10 minutes to a stirred mixture of 3-(3-phenoxyphenyl)propan-1-ol (10.0 g), 1,2-dibromo-1,1,2,2-tetrachloroethane (15.5 g) and diethyl ether (50 cm$^3$) maintained at a temperature within the range 5° to 10° C. After stirring the mixture for a further 45 minutes the precipitate was removed by filtration and the filtrate concentrated by evaporation of the volatile portion under reduced pressure. The residual oil was distilled using a Kugelrohr apparatus (oven temperature 130° C.) at a pressure of 0.1 mm Hg). The colourless distillate consisted of 3-(3-bromopropyl)diphenyl ether (7.0 g, 96% pure by gas-liquid chromatography.

$^1$H NMR (CDCl$_3$) δ: 2.2 (m, 2H); 2.8 (m, 2H); 3.4 (t, 2H); 6.75–7.9 (m, 9H)

Infra red (liquid film): 1586, 1488, 1446, 1256, 1220, 697 cm$^{-1}$

Stage 6: Preparation of 3-(3-phenoxyphenyl)propyl triphenyl phosphonium bromide.

A mixture of 3-(3-bromopropyl)diphenyl ether (1, 0 g), triphenylphosphine (0.9 g) and dry toluene (25 cm$^3$) was heated at the reflux temperature for 36 hours. After cooling, the liquid was separated from the precipitated solid by careful decantation. The solid was washed with toluene (×4), suspended in toluene and the suspension evaporated to dryness under reduced pressure to yield 3-(3-phenoxyphenyl)propyl triphenyl phosphonium bromide (0.88 g).

¹H NMR (CDCl₃/DMSO) δ: 1.95 (broad s, 2H); 2.8 (broad t, 2H); 3.6 (broad m, 2H); 6.7–7.4 (m, 9H); 7.6–7.9 (m, 15H).

EXAMPLE 11

3-(4-Fluoro-3-phenoxyphenyl)propyl triphenyl phosphonium bromide was prepared from 4-fluoro-3-phenoxybenzaldehyde by a multi-stage procedure similar to that described in Example 10.

¹H NMR (DMSO) δ (ppm): ca 1.8 (2H, broad m); ca 2.7 (2H, broad m); ca 3.5 (2H, broad m); 6.9–7.45 (8H, m); 7.6–8.0 (15H, m)

Details for intermediates:

(i) Methyl E-3-(4-fluoro-3-phenoxyphenyl)propenoate:
¹H NMR (CDCl₃) δ (ppm): 3.8 (3H, s); 6.28, 7.66 (2H, ABq, J=16 Hz); 6.9–7.5 (8H, m).

(ii) Methyl 3-(4-fluoro-3-phenoxyphenyl)propanoate:
60 MHz ¹H NMR (CDCl₃) δ (ppm): 2.3–3.0 (4H, m); 3.6 (3H, s); 6.8–7.5 (8H, m)

(iii) 3-(4-Fluoro-3-phenoxyphenyl)propan-1-ol:
60 MHz ¹H NMR (CDCl₃) δ (ppm): ca 1.9 (2H, m); ca 2.55 (2H, m); 3.57 (2H, t); 6.8–7.5 (8H, m).

(iv) 3-(4-Fluoro-3-phenoxyphenyl)-1-bromopropane.
60 MHz ¹H NMR (CDCl₃) δ (ppm): ca 2.1 (2H, m); ca 2.7 (2H, m); 3.35 (2H, t); 6.8–7.5 (8H, m).

EXAMPLE 12

This Example illustrates the preparation of E,Z-2-(4-ethoxyphenyl)-5-(3-phenoxyphenyl)-1,1,1-trifluoropent-2-ene.

n-Butyllithium (0.65 cm³ of a 2.5M solution in hexane) was added to a stirred slurried mixture of 3-(3-phenoxyphenyl)propyl triphenyl phosphonium bromide (0.88 g) and dry tetrahydrofuran (5.0 cm³) maintained at 0° C., and the mixture developed a bright orange colour. After 45 minutes a solution of 4-ethoxy-α,α,α-trifluoroacetophenone (0.35 g) in dry tetrahydrofuran (3.0 cm³) was added to the mixture, at 0° C. after which the mixture was warmed to the ambient temperature over a 30 minute period. The mixture was then poured into water and extracted with chloroform.

The extracts were washed with water, dried over anhydrous magnesium sulphate and concentrated by evaporation of the solvent under reduced pressure. The residual oil was purified by column chromatography using a silica gel column eluted with a 1:10 mixture by volume of ethylacetate and hexane to give a 4:1 mixture of the E and Z isomers of 2-(4-ethoxyphenyl)-5-(3-phenoxyphenyl)-1,1,1-trifluoropent-2-ene as a colourless oil (0.51 g, 96% by gas-liquid chromatography, retention times 11.02 minutes (E-isomer) and 11.59 minutes (Z-isomer).

The product was freed from a minor amount of 4-ethoxy-α,α,α-trifluoroacetophenone by heating in a Kugelrohr apparatus at 100° C./0.1 mm Hg.

¹H NMR (CDCl₃)δ: 1.42 (t, 3H); 2.2–2.8 (m, 4H); 4.04 (q, 2H); 5.95 (m, 0.2H, Z-isomer); 6.4 (m, 0.8H, E-isomer); 6.75–7.4 (m, 13H)

EXAMPLE 13

By the use of a procedure similar to that set out in Example 12 hereinbefore the following compounds were prepared from the appropriate intermediates as follows:

(i) 2-[4-(2-methylprop-2-yl)phenyl]-5-(3-phenoxyphenyl)-1,1,1-trifluoropent-2-ene as a 4:1 mixture of E and Z isomers, from 3-(3-phenoxyphenyl)propyl triphenyl phosphonium bromide and 4-(2-methylprop-2-yl)-α,α,α-trifluoroacetophenone. The product was obtained as a colourless oil which crystallised on standing.

¹H NMR (CDCl₃) δ: 1.34 (s, 9H); 2.2–2.4 (m, 2H); 2.6–2.8 (m, 2H); 6.0, 6.4 (2t, 1H); 6.75–7.4 (m, 13H)

Infra red (liquid film): 1585, 1490, 1305–1120, 835, 695 cm⁻¹

(ii) 5-(3-phenoxyphenyl)-2-(4-trifluoromethoxyphenyl)-1,1,1-trifluoropent-2-ene as a 1:1 mixture of E and Z isomers, from 4-trifluoromethoxy-α,α,α-trifluoroacetophenone and 3-(3-phenoxyphenyl)propyl triphenyl phosphonium bromide. The product was obtained as an oil.

¹H NMR (CDCl₃) δ: 2.3 (q, 1H); 2.68 (t, 1H); 2.78 (m, 2H); 6.0 (t, 0.5H, Z-isomer); 6.44 (t, 0.5H, E-isomer); 6.7–7.4 (m, 13H)

Infra red (liquid film): 1590, 1515, 1490, 1120–1305, 700 cm⁻¹

¹⁹F NMR (CDCl₃) δ (ppm—relative to CFCl₃): −57.98 (CF₃, s—Z isomer) −66.48 (CF₃, s—E isomer) −58.26, −58.34 (OCF₃, 2s)

(iii) 3-(4-ethoxyphenyl)-1,1,1,2,2-pentafluoro-6-(3-phenoxyphenyl)hex-3-ene as a 33:5 mixture of E and Z isomers from 4-ethoxypentafluoropropiophenone and 3-(3-phenoxyphenyl)propyl triphenyl phosphonium bromide. The product was purified by column chromatography using a silica gel column eluted with a hexane-ethyl acetate mixture (25:1), and obtained as a colourless oil.

¹H NMR (CDCl₃) δ: 1.4 (t, 3H); 2.3 (m, 2H); 2.7 (m, 2H); 4.0 (q, 2H); 6.05, 6.4 (2t, 1H); 6.7–7.4 (m, 13H)

(iv) 5-(3-phenoxyphenyl)-1,1,1-trifluoro-2-(4-trifluoromethylphenyl)pent-2-ene as a 2:3 mixture of E and Z isomers, from 4-trifluoroacetylbenzotrifluoride (commercially available from Peboc Ltd, Llangefni, Anglesey, Wales, UK), and 3-(3-phenoxyphenyl)propyl triphenyl phosphonium bromide.

¹H NMR (CDCl₃) δ: ca 2.3, 2.7 (m, 4H); 6.07 (t, 0.6H, Z-isomer); 6.48 (dt, 0.4H, E-isomer); 6.7–7.8 (m, 13H)

(v) 1,1,1-Trifluoro-2-(4-chlorophenyl)-5-(3-phenoxyphenyl)pent-2-ene as a 55:45 mixture of E and Z isomers, from 4-chloro-α,α,α-trifluoroacetophenone and 3-(3-phenoxyphenyl)propyl phosphonium bromide.

¹H NMR (CDCl₃) δ (ppm): 6.7–7.4 (13H, m); E isomer peaks at 2.3(m), 2.66 (t), Z isomer peaks at 2.6–2.8(m)—(total 4H); 6.0 (t, Z isomer) and 6.42 (broad t, E-isomer)(total 1H)

(vi) 1,1,1-Trifluoro-2-(4-methoxymethylphenyl)-5-(3-phenoxyphenyl)-pent-2-ene, as a 7:3 mixture of E:Z isomers, from 4-methoxymethyl-α,α,α-trifluoroacetophenone and 3-(3-phenoxyphenyl)propyl triphenyl phosphonium bromide.

¹H NMR (CDCl₃) δ: 2.3 and 2.6–2.8 (4H, m); 3.38, 3.41 (3H, 2s in ratio 3:7); 4.45 (2H, s); 6.0, 6.4 (total 1H, 2t in ratio 3:7); 6.7–7.4 (13H, m)

¹⁹F NMR (CDCl₃) δ (ppm—relative to CFCl₃): −57.9, −66.4 (2s in ratio 3:7).

(vii) 1,1,1-Trifluoro-2-(3-fluoro-4-ethoxyphenyl)-5-(3-phenoxyphenyl)-pent-2-ene as a 5:3 mixture of E and Z isomers, from 3-fluoro-4-ethoxy-α,α,α-trifluoroacetophenone and 3-(3-phenoxyphenyl)propyl triphenyl phosphonium bromide.

¹H NMR (CDCl₃) δ: ca 1.45 (3H, overlapping triplets); 2.3, 2.7 (4H, m); 4.1 (2H, q); 5.98, 6.40 (1H, 2t in ratio 3:5); 6.7–7.4 (12H, m).

(viii) 1,1,1-Trifluoro-2-(3,5-difluoro-4-ethoxyphenyl)-5-(3-phenoxyphenyl)pent-2-ene as a 4:5 mixture of E and Z isomers from 3,5-difluoro-4-ethoxy-α,α,α-trifluoroacetophenone and 3-(3-phenoxyphenyl)propyl triphenyl phosphonium bromide.

¹H NMR (CDCl₃) δ: 1.4 (3H, 2 overlapping triplets); ca 2.3 and 2.7 (4H, m); 4.23 (2H, m); 6.0, 6.4 (1H); 6.6–7.4 (11H, m).

(ix) 1,1,1-Trifluoro-2-[3,4-(methylmethylenedioxy)-phenyl]-5-(3-phenoxyphenyl)pent-2-ene as a 7:3 mixture of E and Z isomers, from 3,4-(methylmethylenedioxy)-α,α,α-trifluoroacetophenone and 3-(3-phenoxyphenyl)-propyl triphenyl phosphonium bromide.

¹H NMR (CDCl₃) δ: ca 1.7 (3H, 2 overlapping); ca 2.3, 2.6–2.8 (4H, m); 5.96, 6.4 (1H, ratio 3:7); 6.3 (1H, m); 6.5–7.4 (12H, m)

(x) 1,1,1-Trifluoro-2-[3,4-(dimethylmethylenedioxy)-phenyl]-5-(3-phenoxyphenyl)pent-2-ene as a 3:1 mixture of E and Z isomers, from 3,4-(dimethylmethylenedioxy)-α,α,α-trifluoroacetophenone and 3-(3-phenoxyphenyl)propyl triphenyl phosphonium bromide.

¹H NMR (CDCl₃) δ: ca. 1.7 (6H, 2s in ratio 3:1); 2.3, 2.6–2.8 (4H, m); 5.96, 6.37 (1H, ratio 1:3); 6.5–7.4 (12H, m).

(xi) 1,1,1-Trifluoro-2-(4-methoxyphenyl)-5-(3-phenoxyphenyl)pent-2-ene as a 4:1 mixture of E and Z isomers, from 4-methoxy-α,α,α-trifluoroacetophenone and 3-(3-phenoxyphenyl)propyl triphenyl phosphonium bromide ¹H NMR (CDCl₃) δ: 2.3, 2.6–2.8 (4H, m); 3.8 (3H, s); 5.95, 6.4 (1H, 2 broad triplets, in ratio 1:4); 6.7–7.4 (13H, m)

(xii) 1,1,1-Trifluoro-2-(4-trifluoromethoxyphenyl)-5-(4-fluoro-3-phenoxyphenyl)pent-2-ene as a 1:1 mixture of E and Z isomers, from 4-trifluoromethoxy-α,α,α-trifluoroacetophenone and 3-(4-fluoro-3-phenoxyphenyl)-propyl triphenyl phosphonium bromide.

¹H NMR (CDCl₃) δ (ppm): 2.3, 2.6–2.8 (4H, m); 5.98 (0.5H, broad t); 6.42 (0.5M, broad t); 6.7–7.4 (12H, m).

¹⁹F NMR (CDCl₃) δ (ppm—relative to CFCl₃): −58.0 (CF₃—Z isomer); −58.28, −58.37 (CF₃O, 2s) −66.52 (CF₃—E isomer); −134.7 (1F, m).

(xiii) 1,1,1-Trifluoro-2-(4-bromophenyl)-5-(3-phenoxyphenyl)-pent-2-ene as a 1:1 mixture of E and Z isomers from 4-bromo-α,α,α-trifluoroacetophenone and 3-(3-phenoxyphenyl)propyl triphenyl phosphonium bromide.

¹H NMR (CDCl₃) δ (ppm): 2.26, 2.6–2.8 (4H, m); 5.98, 6.4 (each 0.5H, t); 6.7–7.5 (13H, m).

¹⁹F NMR (CDCl₃) δ (ppm—relative to CFCl₃): −57.96, −66.48 CF₃, s).

(xiv) 1,1,1-Trifluoro-2-(4-fluorophenyl)-5-(3-phenoxyphenyl)pent-2-ene, as a 55:45 mixture of E and Z isomers from 4-fluoro-α,α,α-trifluoroacetophenone (commercially available from Peboc Ltd, Llangefni, Anglesey, Wales, UK,) and 3-(3-phenoxyphenyl)propyl triphenyl phosphonium bromide.

¹H NMR (CDCl₃) δ (ppm): 2.27, 2.6–2.8 (4H, m); 5.98 (0.45H, m, Z isomer); 6.4 (0.55H, m, E-isomer); 6.7–7.4 (13H, m).

¹⁹F NMR (CDCl₃) δ (ppm—relative to CFCl₃): −58.1 (CF₃, s, Z-isomer); −66.7 (CF₃, s, E-isomer); ca −114 (1F, m).

(xv) 1,1,1-Trifluoro-2-(5-indanyl)-5-(3-phenoxyphenyl)pent-2-ene, as a 3:1 mixture of E and Z isomers from 5-trifluoroacetylindane (commercially available from Peboc Ltd, Llangefni, Anglesey, Wales, UK) and 3-(3-phenoxyphenyl)propyl triphenyl phosphonium bromide.

¹H NMR (CDCl₃) δ (ppm): 2.0–2.4, 2.6–3.0 (10H, m); 5.97 (0.25H, m, Z-isomer); 6.4 (0.75H, m, E-isomer); 6.7–7.4 (12H, m).

¹⁹F NMR (CDCl₃) δ (ppm—relative to CFCl₃): −57.86 (CF₃, s, Z-isomer); −66.42 (CF₃, s, E-isomer) (1:3 ratio).

(xvi) 1,1,1-Trifluoro-2-(3,4-methylenedioxyphenyl)-5-(3-phenoxyphenyl)pent-2-ene, as a 1:2 mixture of E and Z isomers from 3,4-methylenedioxy-α,α,α-trifluoroacetophenone and 3-(3-phenoxyphenyl)propyl-triphenyl phosphonium bromide.

¹H NMR (CDCl₃) δ (ppm): 2.35 (1.33H, m); 2.7 (2H, t); and (0.67H, m); 6.0 (2H, s); and (0.33H, m); 6.4 (0.67H, t); 6.5 (1H, s); 6.7–7.4 (11H, m).

(xvii) 1,1-Difluoro-2-(4-trifluoromethoxyphenyl)-5-(4-fluoro-3-phenoxyphenyl)pent-2-ene, 10:1 mixture of E and Z isomers, obtained as a by-product of Example 31 (xxix).

¹H NMR (CDCl₃) δ (ppm): ca 2.3 (2H, m); 2.64 (2H, t); ca. 6.04 (1H, m); 6.11 (1H, t, J=56 Hz); 6.7–7.4 (12H, m).

¹⁹F NMR (CDCl₃) δ (ppm—relative to CFCl₃): −58.28 (CF₃O, s); −58.38 (CF₃O, s Z isomer); −111.9 (CF₂H, m, E-isomer); −113.3 (CF₂H, m, Z-isomer).

Ratio of E:Z isomers, 10:1.

EXAMPLE 14

This Example illustrates the separation of the E and Z isomers of 1,1,1-trifluoro-2-(4-ethoxyphenyl)-5-(3-phenoxyphenyl)-pent-2-ene.

A 4:1 mixture of the E and Z isomers of the title compound (0.25 g) was separated by repeated injection onto a semipreparative high pressure liquid chromatographic column containing a silica gel support, eluting with n-hexane containing 0.5% by volume of ethyl acetate. The first fraction was the major isomer, identified as E-1,1,1-trifluoro-2-(4-ethoxyphenyl)-5-(3-phenoxyphenyl)pent-2-ene (0.15 g).

¹H NMR (CDCl₃) δ: 1.41 (3H, t); 2.3 (2H, t); 4.03 (2H, q); 6.4 (1H, broad t); 6.7–7.4 (13H, m)

¹⁹F NMR (CDCl₃) δ (ppm—relative to CFCl₃): −66.5

The slower running fraction was identified as Z-1,1,1-trifluoro-2-(4-ethoxyphenyl)-5-(3-phenoxyphenyl)pent-2-ene (0.45 g).

¹H NMR (CDCl₃) δ: 1.41 (3H, t); 2.65–2.85 (4H, m); 4.03 (2H, q); 5.96 (1H, t); 6.8–7.4 (13H, m).

¹⁹F NMR (CDCl₃) δ (ppm—relative to CFCl₃): −57.98

EXAMPLE 15

This Example illustrates the stages in the preparation of 2,3,4,5,6-pentafluorobenzyl triphenyl phosphonium bromide Stage 1: Preparation of 2,3,4,5,6-pentafluorobenzylbromide A mixture of phosphorus tribromide (2.1 g) and toluene (1 cm³) was added dropwise to a solution of 2,3,4,5,6-pentafluorobenzylalcohol (3.4 g) and pyridine (0.21 g) in toluene (10 cm³) at 0° C. The reaction mixture was stirred at 0° C. for 45 minutes, then at the ambient temperature (ca. 20° C.) for 75 minutes, and was then added to an excess of saturated sodium bicarbonate solution. The products were extracted into diethyl ether, and the combined ether layers dried and concentrated by evaporation under reduced pressure. The residual solution (still containing toluene) was passed through a plug of silica gel.

The solution of 2,3,4,5,6-pentafluorobenzyl bromide was used without further isolation or purification of the product.

Stage 2: Preparation of 2,3,4,5,6-pentafluorobenzyl triphenyl phosphonium bromide.

The toluene solution from Stage 1 was mixed with triphenyl phosphine (1 g) and heated at 130° C. for 3 hours. After cooling, the solution was diluted with diethyl ether (5 cm$^3$) and the title compound filtered off, washed with hexane (4×5 cm$^3$) and dried by suction.

EXAMPLE 16

The following compounds were prepared from the appropriate starting materials by a procedure similar to that described in Example 15.

(i) α-Cyano-3-phenoxybenzyltriphenylphosphonium bromide from α-cyano-3-phenoxybenzyl alcohol.

$^1$H NMR (CDCl$_3$) of intermediate α-cyano-3-phenoxybenzyl bromide

δ (ppm): 5.3 (1H, s); 6.8–7.4 (9H, m)

(ii) α-Methyl-3-phenoxybenzyltriphenylphosphonium bromide from α-methyl-3-phenoxybenzyl alcohol.

(iii) 6-Phenoxypyrid-2-ylmethyltriphenylphosphonium bromide from 6-phenoxypyrid-2-ylmethyl alcohol.

$^1$H NMR (CDCl$_3$) of intermediate 6-phenoxypyrid-2-ylmethyl bromide.

δ (ppm): 4.40 (2H, s); 6.75 (1H, d); 7.2–7.7 (7H, m).

(iv) 3-Phenoxybenzyltriphenylphosphonium bromide from 3-phenoxybenzyl alcohol.

(v) 4-Fluoro-3-phenoxybenzyltriphenylphosphonium bromide from 4-fluoro-3-phenoxybenzyl alcohol.

EXAMPLE 17

This Example illustrates the stages in the preparation of E,Z-1,1,1-trifluoro-2-(4-ethoxyphenyl)-5-(3-phenoxyphenyl)pent-4-ene.

Stage 1: Preparation of methyl E-3-(4-ethoxyphenyl)-4,4,4-trifluorobut-2-enoate

A solution of 4-ethoxy-trifluoroacetophenone (2.0 g, 9.2×10$^{-3}$ moles) in tetrahydrofuran (60 cm$^3$) at 25° C. was treated with (carbomethoxymethylene)triphenylphosphorane (6.1 g, 18.3×10$^{-3}$ moles). The resulting solution was stirred at 25° C. for 3 hours, silica (8 g) was added and the solvent removed. The resulting slurry was chromatographed (eluted with 10% ether in petroleum ether) to give the desired product as a colourless oil (2.4 g, 95%).

$^1$H NMR (CDCl$_3$) δ (ppm): 1.41 (t, 3H); 3.61 (s, 3H); 4.02 (q, 2H); 6.59 (q, 1H); 6.92 (d, 2H); 7.21 (d, 2H).

Stage 2: Preparation of methyl 3-(4-ethoxyphenyl)-4,4,4-trifluorobutanoate

A mixture of methyl E-3-(4-ethoxyphenyl)-4,4,4-trifluorobut-2-enoate (2.4 g, 8.8×10$^{-3}$ moles) and 5% palladium on carbon (500 mg) in ethanol (50 cm$^3$) was rapidly stirred under hydrogen (three atmospheres) for two hours. The catalyst was filtered off and the solvent removed to leave a colourless oil. Chromatographic purification allowed the isolation of the desired product (2.3 g, 96%).

$^1$H NMR (CDCl$_3$) δ (ppm): 1.40 (t, 3H); 2.85 (dd, 1H); 2.95 (dd, 1H); 3.60 (s, 3H); 3.85 (m, 1H); 4.2 (q, 2H); 6.84 (d, 2H); 7.20 (d, 2H).

Stage 3: Preparation of 3-(4-ethoxyphenyl)-4,4,4-trifluorobutanal

To a solution of methyl 3-(4-ethoxyphenyl)-4,4,4-trifluorobutanoate (2.0 g, 7.2×10$^{-3}$ moles) in toluene (25 cm$^3$) at −78° C. was added one molar diisobutylaluminium hydride (7.2 ml, 7.2×10$^{-3}$ moles) in toluene. The resulting solution was stirred at −78° C. for two hours before quenching the reaction by the sequential addition of acetic acid (0.48 cm$^3$, 8.4×10$^{-3}$ moles), water (1 cm$^3$) and sodium sulphate (10 g). The resulting slurry was allowed to warm to room temperature and after a further twenty minutes stirring the solids were filtered off through a silica plug. The solvent was removed to leave a colourless oil which was characterised as the title compound.

$^1$H NMR (CDCl$_3$) δ (ppm): 1.4 (t, 3H); 3.0 (bd, 2H); 3.85 (m, 1H); 4.0 (q, 2H); 6.85 (d, 2H); 7.20 (d, 2H); 9.60 (bs, 1H)

Stage 4: Preparation of 1,1,1-trifluoro-2-(4-ethoxyphenyl)-5-(3-phenoxyphenyl)pent-4-ene as a 6:4 mixture of E and Z isomers A suspension of 3-phenoxybenzyl triphenyl phosphonium bromide (3.0 g, 5.72×10$^{-3}$ moles) in tetrahydrofuran (10 cm$^3$) at 0° C. was treated with 2.5M n-butyl lithium (2.30 cm$^3$), 5.72×10$^{-3}$ moles). The resulting solution was stirred for twenty minutes then added dropwise to a solution of 3-(4-ethoxyphenyl)-4,4,4-trifluorobutanal (1.0 g, 4.1×10$^{-3}$ moles) in tetrahydrofuran (10 cm$^3$) at 0° C. over five minutes. After twenty minutes water (10 cm$^3$) was added and the product extracted into diethyl ether (3×20 cm$^3$). Evaporation of the solvent followed by silica chromatography (eluted with 10% ether in petroleum ether) allowed isolation of the title compounds (60% E:40% Z, 750 mg. 47%).

$^1$H NMR (CDCl$_3$)δ: 1.41 (t, 3H), 2.70–3.00 (m, 2H); 3.35 (m, 1H); 4.01 (q, 2H); 5.40 (dt, 0.4H), Z-isomer); 5.95 (dt, 0.6H, E-isomer); 6.39 (2d, 1H); 6.85–7.0 (m, 13H).

EXAMPLE 18

The following compounds were prepared from the appropriate starting materials by a procedure similar to that described in Example 17.

(i) 1,1,1-Trifluoro-2-(4-ethoxyphenyl)-5-(4-fluoro-3-phenoxyphenyl)pent-4-ene as a 6:4 mixture of E and Z isomers, from 3-(4-ethoxyphenyl)-4,4,4-trifluorobutanal and 4-fluoro-3-phenoxybenzyl triphenyl phosphonium bromide.

$^1$H NMR (CDCl$_3$) δ: 1.40 (3H, t); 2.7–2.9 (2H, m); 3.35 (1H, m); 4.0 (2H, q); 5.39 (dt, 0.4H-Z-isomer); 5.9 (dt, 0.6H, E-isomer); 6.35 (2d, 1H); 6.8–7.4 (12H, m).

(ii) 1,1,1-Trifluoro-2-(4-ethoxyphenyl)-5-cyano-5-(3-phenoxyphenyl)pent-4-ene from 3-(4-ethoxyphenyl)-4,4,4-trifluorobutanal and α-cyano-3-phenoxybenzyltriphenyl phosphonium bromide.

Obtained in only 30% purity on work-up. Crude product used without purification in hydrogenation reaction.

(iii) 1,1,1-Trifluoro-2-(4-ethoxyphenyl)-5-(3-phenoxyphenyl)hex-4-ene from 3-(4-ethoxyphenyl)-4,4,4-trifluorobutanal and α-methyl-3-phenoxybenzyl triphenyl phosphonium bromide.

$^1$H NMR (CDCl$_3$) δ (ppm): 1.4 (3H, t); 1.95 (3H, s); 2.75 (2H, m); 3.15 (1H, m); 4.0 (2H, q); 5.5 (1H, t); 6.8–7.25 (13H, m).

(iv) 1,1,1-Trifluoro-2-(4-ethoxyphenyl)-5-(pentafluorophenyl)pent-4-ene as a 2:1 mixture of E and Z isomers, from 3-(4-ethoxyphenyl)-4,4,4-trifluorobutanal and 2,3,4,5,6-pentafluorobenzyl triphenylphosphonium bromide.

¹H NMR (CDCl₃) δ (ppm): 1.4 (3H, t); 2.4-2.8 (2H, m); 3.3 (1H, m); 4.0 (2H, q); 5.8 (1H, m); 6.0 (0.67H, broad); 6.25 (0.33H, broad s); 6.8-7.2 (4H, m).

(v) 1,1,1-Trifluoro-2-(4-ethoxyphenyl)-5-(6-phenoxypyrid-2-yl)pent-4-ene, as a 3:1 mixture of E and Z isomers from 3-(4-ethoxyphenyl)-4,4,4-trifluorobutanal and 6-phenoxypyrid-2-ylmethyl triphenyl phosphonium bromide.

¹H NMR (CDCl₃) δ (ppm): 1.4 (3H, t); 1.7-2.0 (2H, m); 3.35 (1H, m); 4.0 (2H, m); 5.4 (0.25H, m); 6.2 (0.25H, m); 6.4 (1.5H, m); 6.6 (1H, d); 6.8-7.6 (11H, m).

EXAMPLE 19

This Example illustrates the separation of the E and Z isomers of 1,1,1-trifluoro-2-(4-ethoxyphenyl)-5-(3-phenoxyphenyl)pent-4-ene.

Separation was performed by high pressure liquid chromatography on a silica gel column, eluting with hexane containing 0.5% by volume ethyl acetate.

Z-isomer:
¹H NMR (CDCl₃) δ (ppm): 1.4 (3H, t); 2.8-3.0 (2H, m); 3.3 (1H, m); 4.0 (2H, q); 5.4 (1H, m); 6.4 (1H, d, J=11.5 Hz); 6.8-7.4 (13H, m).

E-isomer:
¹H NMR (CDCl₃) δ (ppm): 1.4 (3H, t); 2.8-3.0 (2H, m); 3.3 (1H, m); 4.0 (3H, q); 5.8-6.0 (1H, m); 6.4 (1H, d, J=15.8 Hz); 6.8-7.4 (13H, m).

EXAMPLE 20

This Example illustrates the stages in the preparation of 1,1,1-trifluoro-2-(4-ethoxyphenyl)-5-(4-fluoro-3-phenoxyphenyl)penta-2,4-diene Stage 1: Preparation of E-3-(4-ethoxyphenyl)-4,4,4-trifluorobut-2-enal To a solution of methyl E-3-(4-ethoxyphenyl)-4,4,4-trifluorobut-2-enoate, prepared according to Example 17, stage 1, (1.5 g, 5.5×10⁻³ moles) in toluene (20 ml) at −78° C. was added dropwise one molar equivalent of diisobutylaluminium hydride (5.5 ml, 5.5×10⁻³ moles) in toluene. The resulting solution was stirred at −78° C. for two hours before quenching the reaction by the sequential addition of acetic acid (0.40 ml, 7.0×10⁻³ moles), water (1 ml) and sodium sulphate (10 g). The resulting slurry was allowed to warm to room temperature and after a further twenty minutes stirring the solids were filtered off through silica. After removal of the solvent the crude aldehyde was purified by silica chromatography (eluted with 10%, in petroleum ether to give the title compound (0.87 g, 65%).

60 MHz ¹H NMR (CDCl₃) δ: 1.40 (t, 3H); 4.10 (q, 2H); 6.50 (d, 1H); 6.91 (d, 2H); 7.20 (d, 2H); 9.45 (d, 1H).

Stage 2: Preparation of 1,1,1-trifluoro-2-(4-ethoxyphenyl)-5-(4-fluoro-3-phenoxyphenyl)penta-2,4-diene as a 1:1 mixture of the 2E, 4E and 2E, 4Z isomers.

The title compound was prepared by the reaction of 4-fluoro-3-phenoxybenzyl triphenyl phosphonium bromide with E-3-(4-ethoxyphenyl)-4,4,4-trifluorobut-2-enal according to the method described in Example 17, stage 4.

¹H NMR (CDCl₃) δ: 1.42 (2H, d); 4.05 (2H, m); 6.18 (dd, 0.5H); 6.45-6.80 (m, 2.5H); 6.90-7.40 (12H, m).

Isomers separated by high pressure liquid chromatography on silica gel, eluting with hexane containing 0.66% by volume ethyl acetate.

(2E, 4E) isomer:
¹H NMR (CDCl₃) δ (ppm): 1.4 (3H, t); 4.05 (2H, q); 6.5-6.6 (1H, m); 6.75 (1H, d, J=16 Hz); 6.8-7.4 (13H, m).

(2E, 4Z) isomer:
¹H NMR (CDCl₃) δ (ppm): 1.4 (3H, t); 4.05 (2H, q); 6.2 (1H, dd); 6.6 (1H, d, J=12 Hz); 6.8-7.4 (13H, m).

EXAMPLE 21

The following compounds were prepared by a procedure similar to that described in Example 20.

(i) 1,1,1-Trifluoro-2-(4-ethoxyphenyl)-5-(6-phenoxypyrid-2-yl)penta-2,4-diene as a 9:1 (approximately) mixture of Z isomers, from E-3-(4-ethoxyphenyl)-4,4,4-trifluorobut-2-enal and 6-phenoxypyrid-2-ylmethyl triphenyl phosphonium bromide.

Stereochemistry of the two isomers not assigned due to complexity of the spectral data.

¹H NMR (CDCl₃) δ (ppm): 1.4 (0.3H and 0.27H, m); 4.0 (0.2H and 0.18H, m); 5.2-5.7 (15H, m).

EXAMPLE 22

This Example illustrates the stages in the preparation of 3-(4-fluoro-3-phenoxyphenyl)prop-2-en-1-yl triphenyl phosphonium chloride.

Stage 1: Preparation of 1-(4-fluoro-3-phenoxyphenyl)-prop-2-en-1-ol

A solution of 4-fluoro-3-phenoxybenzaldehyde (35 g) in dry tetrahydrofuran (100 cm³) was added slowly to stirred vinyl magnesium bromide, commercially available from the Aldrich Chemical Co Ltd, Gillingham, Dorset, England, (162 cm³ of a 1.0 molar solution in tetrahydrofuran) under an atmosphere of nitrogen at the ambient temperature (ca 20° C.); a moderate exotherm was noted, raising the temperature of the mixture to 40° C. On completion of the addition, the mixture was stirred for a further 2 hours, then poured into water and acidified with dilute hydrochloric acid. The products were extracted three times into ethyl acetate and the combined organic layers were washed with water, dried over anhydrous magnesium sulphate and concentrated by evaporation under reduced pressure to give a viscous oil (39 g), characterised as 1-(4-fluoro-3-phenoxyphenyl)prop-2-en-1-ol, 97% pure by gas liquid chromatographic analysis.

400 MHz ¹H NMR (CDCl₃) δ (ppm): ca 2.3 (1H, broad); 5.11 (1H, dd, J=10 Hz, 1 Hz); 5.18 (1H, dt, J=10 Hz, 1 Hz); 5.3 (1H, dt, J=17 Hz, 1 Hz); ca 5.95 (1H, m); 6.9-7.4 (8H, m).

Stage 2: Preparation of E-3-(4-fluoro-3-phenoxyphenyl-1-chloroprop-2-ene 1-(4-Fluoro-3-phenoxyphenyl)prop-2-en-1-ol (38 g) was dissolved in tetrahydrofuran (400 cm³) and concentrated hydrochloric acid (180 cm³) was added with vigorous stirring. Stirring was continued for a further 2 hours, after which time, analysis of a withdrawn sample by gas liquid chromatography showed no starting material remaining. The mixture was diluted with water and the products extracted into ethyl acetate. The combined organic layers were washed with water (4 times), then dried over anhydrous magnesium sulphate. Evaporation of the solvent under reduced pressure gave E-3-(4-fluoro-3-phenoxyphenyl)-1-chloroprop-2-ene (44 g) as a viscous oil, 98% pure by gas liquid chromatographic analysis.

¹H NMR (CDCl₃) δ (ppm): 4.19 (2H, d); ca 6.15 (1H, dt); ca 6.55 (1H, d); 6.9-7.4 (8H, m).

The E configuration was assigned after consideration of the coupling constants in the NMR spectrum.

Stage 3: Preparation of 3-(4-fluoro-3-phenoxyphenyl)prop-2-en-1-yl triphenyl phosphonium chloride.

A mixture of E-3-(4-fluoro-3-phenoxyphenyl)-1-chloroprop-2-ene (42 g), triphenylphosphine (42 g) and xylene (300 cm³) was heated at the reflux temperature for 16 hours. After cooling, crystals of 3-(4-fluoro-3-phenoxyphenyl)prop-2-en-1-yl triphenyl phosphonium chloride (68 g) were filtered from the reaction mixture, washed with dry diethyl ether, dried by suction and stored in a desiccator under vacuum.

¹H NMR (DMSO) δ (ppm): ca 4.65 (2H, m); 6.0 (1H, broad m); 6.55 (1H, dd); 6.9–7.4 (8H, m); 7.7–7.9 (15H, m).

EXAMPLE 23

The following compounds were prepared by a procedure similar to that described in Example 22.

(i) 3-(4-Fluoro-3-benzylphenyl)prop-2-en-1-yl triphenyl phosphonium chloride, from 4-fluoro-3-benzylbenzaldehyde (The preparation of 4-fluoro-3-benzylbenzaldehyde is described in Example 42).

NB. In this Example, the addition of the aldehyde solution to vinyl magnesium bromide in stage 1 was performed at 5° C.

¹H NMR (CDCl₃) δ (ppm): 3.90 (2H, s); 5.1 (2H, dd); 5.8 (1H, m); 6.65 (1H, dd); 6.8–7.9 (23H, m).

(ii) 3-(3-Phenoxyphenyl)prop-2-en-1-yl triphenyl phosphonium chloride, from 3-phenoxybenzaldehyde.

¹H NMR (CDCl₃) δ (ppm): ca 4.7 (1H, m); ca 6.1 (1H, m); 6.5 (1H, dd); 6.8–7.4 (9H, m); 7.65–7.9 (15H, m).

EXAMPLE 24

This Example illustrate the preparation of 1,1,1-trifluoro-2-(4-trifluoromethoxyphenyl)-5-(3-phenoxyphenyl)penta-2,4-diene as a 6:1 mixture of the 2E, 4E) and (2Z, 4E) isomers.

n-Butyllithium (6.4 cm³ of a 2.5M solution in n-hexane) was added dropwise to a cooled (0° C.) suspension of 3-(3-phenoxyphenyl)prop-2-en-1-yl triphenyl phosphonium chloride (8.2 g) in dry tetrahydrofuran (100 cm³); a dark red colour developed in the reaction mixture. The reaction mixture was stirred at 0° C. for a further 30 minutes, then a solution of 4-trifluoromethoxy-α,α,α-trifluoroacetophenone (3.87 g) in dry tetrahydrofuran (50 cm³) was added dropwise. The mixture was allowed to stir for a further hour and was then poured into water, and the products extracted into diethyl ether. The combined organic layers were washed with water, dried over anhydrous magnesium sulphate and concentrated by evaporation under reduced pressure. The residue was mixed with silica gel and diethyl ether and evaporated. The residue was placed on top of a short plug of silica, and products were eluted by washing with n-hexane containing 10% by volume diethyl ether. Evaporation under reduced pressure gave an oil, which was purified by high pressure liquid chromatography, using n-hexane containing 10% by volume dichloromethane as eluent to give the title compound as a 6:1 mixture of the (2E, 4E) and (2Z, 4E) isomers (4.24 g). High pressure liquid chromatography using n-hexane containing 1% by volume ethyl acetate allowed separation and isolation of the major (2E, 4E) isomer of 96% purity.

¹H NMR (CDCl₃) δ (ppm) for 2E, 4E isomer:
6.55 (1H, dd); 6.8–7.4 (15H, m).

¹⁹F NMR (CDCl₃) δ (ppm—relative to CFCl₃) for isomer mixture:
−56.88 (E isomer CF₃, s); −58.18 and −58.33 (CF₃O, 2s); −65.2 (Z isomer CF₃, s).

EXAMPLE 25

The following compounds were prepared from the appropriate starting materials by a procedure similar to that described in Example 24.

(i) 1,1,1-Trifluoro-2-(4-ethoxyphenyl)-5-(4-fluoro-3-benzylphenyl)penta-2,4-diene, as an 86:14 mixture of the (2E, 4E) and (2Z, 4E) isomers from 4-ethoxy-α,α,α-trifluoroacetophenone and 3-(4-fluoro-3-benzylphenyl)-prop-2-en-1-yl triphenyl phosphonium chloride.

¹H NMR (CDCl₃) δ (ppm): 1.4 (3H, 2t); 4.0–4.15 (2H, 2q); 3.95, 4.0 (2H, s); 6.4–7.4 (15H, m).

(ii) 1,1,1-Trifluoro-2-(4-trifluoromethoxyphenyl)-5-(4-fluoro-3-benzylphenyl)penta-2,4-diene, as an 86:14 mixture of the (2E, 4Z) and 2Z, 4E) isomers, from 4-trifluoromethoxy-α,α,α-trifluoroacetophenone and 3-(4-fluoro-3-benzylphenyl)prop-2-en-1-yl triphenyl phosphonium chloride.

¹H NMR (CDCl₃) δ (ppm): 3.95, 4.0 (2H, 2s); 6.4–7.4 (15H, m)

(iii) 1,1-Difluoro-2-(4-ethoxyphenyl)-5-(3-phenoxyphenyl)penta-2,4-diene, as a 3:1 mixture of the (2E, 4E) and (2Z, 4E) isomers, from 4-ethoxy-α,α-difluoroacetophenone and 3-(3-phenoxyphenyl)prop-2-en-1-yl triphenyl phosphonium chloride.

¹H NMR (CDCl₃) δ (ppm): ca 1.4 (3H, overlapping t); ca 4.1 (2H, overlapping q); 6.26 (1H, t, J=56 Hz); 6.6–7.4 (16H, m)

¹⁹F NMR (CDCl₃) δ (ppm—relative to CFCl₃):
−111.4 and −112.8 overlapping doublets in ratio 3:1. Molecular ion: 392 for both isomers.

(iv) 1,1-Difluoro-1-chloro-2-(4-ethoxyphenyl-5-(3-phenoxyphenyl)penta-2,4-diene as a 4:1 mixture of the (2E, 4E) and (2Z, 4E) isomers, from 4-ethoxy-α,α-difluoro-α-chloroacetophenone and 3-(3-phenoxyphenyl)prop-2-en-1-yl triphenyl phosphonium chloride.

¹H NMR (CDCl₃) δ (ppm): ca 1.45 (3H, overlapping t); ca 4.10 (2H, overlapping q); 6.4–7.4 (16H, m)

¹⁹F NMR (CDCl₃) δ (ppm—relative to CFCl₃):
−43.9, −51.3 (CF₂Cl, 2s, in ratio 1:4)

(NB. Product contained some unreacted acetophenone, which could be removed by heating the product under vacuum).

(v) 1,1,1-Trifluoro-2-(3,5-difluoro-4-trifluoromethoxyphenyl)-5-(3-phenoxyphenyl)penta-2,4-diene as a mixture of (2E, 4E) and (2Z, 4E) isomers from 3,5-difluoro-4-trifluoromethoxy-α,α,α-trifluoroacetophenone and 3-(3-phenoxyphenyl)prop-2-en-1-yl triphenyl phosphonium chloride.

¹H NMR (CDCl₃) δ (ppm): 6.33 (dd); 6.65 (d); 6.8 (d); 6.9–7.4 (m)

Note: This compound was produced in a mixture with the compound of example (vi) below from a mixture of starting acetophenones. The products (v) and (vi) were separated by high pressure liquid chromatography.

(vi) 1,1,1-Trifluoro-2-(2-bromo-4,6-difluoro-5-trifluoromethoxyphenyl)-5-(3-phenoxyphenyl)penta-2,4-diene as a 1:1 mixture of the (2E, 4E) and (2Z, 4E) isomers, from 2-bromo-4,6-difluoro-5-trifluoromethoxy-α,α,α-trifluoroacetophenone and 3-(3-phenoxyphenyl)prop-2-en-1-yl-triphenyl phosphonium chloride.

¹H NMR (CDCl₃) δ (ppm): 6.2 (dd); 6.56 (d); 6.82 (d); 6.9–7.45 (m)

¹⁹F NMR (CDCl₃) (ppm—relative to CFCl₃):
−57.86 (CF₃—Z isomer, d); −65.20 (CF₃—E isomer, d); −60.25, −60.275 (OCF₃, overlapping t); ca −117.4, −121.7 (ring F, overlapping m).

Note: See note for example (v) above.

(vii) 1,1,1-Trifluoro-2-(3,5-difluoro-4-ethoxyphenyl)-5-(4-fluoro-3-phenoxyphenyl)penta-2,4-diene as a 5:1 mixture of the (2E, 4E) and (2Z, 4E) isomers, from 3,5-difluoro-4-ethoxy-α,α,α-trifluoroacetophenone and 3-(4-fluoro-3-phenoxyphenyl)prop-2-en-1-yl triphenyl phosphonium chloride.

400 MHz $^1$H NMR (CDCl$_3$) δ (ppm): 1.40, 1.43 (3H, overlapping t in ratio 1:5), 4.23, 4.3 (2H, overlapping q); 6.4–7.4 (13H, m).

(viii) 1,1,1-Trifluoro-2-(4-trifluoromethoxyphenyl)-5-(4-fluoro-3-phenoxyphenyl)penta-2,4-diene as an 85:15 mixture of the (2E, 4E) and (2Z, 4E) isomers from 4-trifluoromethoxy-α,α,α-trifluoroacetophenone and 3-(4-fluoro-3-phenoxyphenyl)prop-2-en-1-yl triphenyl phosphonium chloride.

The 85:15 isomer mixture was separated by chromatography to give (A) the pure (2E, 4E) isomer and (B) a 1:1 mixture of the (2E, 4E) and (2Z, 4E) isomers.

(A) (2E, 4E) isomer: $^1$H NMR (CDCl$_3$) δ (ppm): 6.45 (1H, dd); 6.78 (1H, d); 6.9–7.4 (13H, m).

(B) contains extra peaks in the alkene region for the Z-isomer (ca 6.65).

(ix) 1,1-Difluoro-1-chloro-2-(4-trifluoromethoxyphenyl)-5-(4-fluoro-3-phenoxyphenyl)penta-2,4-diene as a 12:1 mixture of (2E, 4E) isomers, from 4-trifluoromethoxy-α,α-difluoro-α-chloroacetophenone and 3-(4-fluoro-3-phenoxyphenyl)prop-2-en-1-yl triphenyl phosphonium chloride.

$^1$H NMR (CDCl$_3$) δ (ppm): 6.32 (dd) and 6.77 (d), (2E, 4E isomer); 6.45 (d) and 6.7 (d) (2Z, b 4E isomer); 6.9–7.5 (m).

(x) 1,1-Difluoro-1-chloro-2-(4-trifluoromethoxyphenyl)-5-(3-phenoxyphenyl)penta-2,4-diene as a 13:1 mixture of (2E, 4E) and (2Z, 4E) isomers, from 4-trifluoromethoxy-α,α-difluoro-α-chloroacetophenone and 3-(3-phenoxyphenyl)prop-2-en-1-yl triphenyl phosphonium chloride.

(2E, 4E) isomer separated by high pressure liquid chromatography (93% pure).

$^1$H NMR (CDCl$_3$) δ (ppm): 6.44 (1H, dd); 6.8–7.4 (15H, m).

Molecular ion: 466/468

EXAMPLE 26

This Example describes the preparation of 1,1-difluoro-2-(4-trifluoromethoxyphenyl)-5-(4-fluoro-3-phenoxyphenyl)penta-2,4-diene as a 9:1 mixture of (2E, 4E) and (2Z, 4E) isomers.

1,1-Difluoro-1-chloro-2-(trifluoromethoxyphenyl)-5-(4-fluoro-3-phenoxyphenyl)penta-2,4-diene was reduced with tri-n-butyl tin hydride according to the procedure described in Example 8.

The compound was isolated as a 9:1 mixture of the (2E, 4E) and (2Z, 4E) isomers.

$^1$H NMR (CDCl$_3$) δ (ppm): 6.18 (1H, (CHF$_2$), t, J=54 Hz); 6.4–7.4 (15H, m)

EXAMPLE 27

This Example describes the preparation of 1,1-difluoro-2-(4-trifluoromethoxyphenyl)-5-(3-phenoxyphenyl)penta-2,4-diene as a 5:1 mixture of (2E, 4E) and (2Z, 4E) isomers.

This product was prepared by the reduction of 1,1-difluoro-1-chloro-2-(4-trifluoromethoxyphenyl)-4-(3-phenoxyphenyl)-penta-2,4-diene with tri-n-butyl tin hydride according to the procedure described in Example 8.

The compound was isolated as a 5:1 mixture of the (2E, 4E) and (2Z, 4E) isomers following purification by column and high pressure liquid chromatography.

$^1$H NMR (CDCl$_3$) δ (ppm): 6.27 (1H, t, J=54 Hz); 6.6–7.4 (16H, m).

Molecular ion 432

EXAMPLE 28

This Example illustrates the preparation of E-dimethyl 3-(4-fluoro-3-phenoxyphenyl)prop-2-en-1-yl)phosphonate.

A mixture of 3-(4-fluoro-3-phenoxyphenyl)-1-chloroprop-2-ene (1 g) and trimethyl phosphite (0.95 g) was heated at 125° C. under an atmosphere of nitrogen for 6 hours. Analysis by gas liquid chromatography showed complete reaction at this stage. The mixture was cooled and poured into water, and the products were extracted into chloroform. The combined organic layers were washed twice with water, dried over anhydrous magnesium sulphate and concentrated to leave 3-(4-fluoro-3-phenoxyphenyl)prop-2-en-1-yl phosphonate as an oil (1.3 g).

$^1$H NMR (CDCl$_3$) δ (ppm): 2.73 (2H, dd and fine coupling); 3.74 (6H, d); 6.0 (1H, m); 6.42 (1H, dd); 6.9–7.4 (8H, m).

EXAMPLE 29

This Example describes the preparation of 1,1-difluoro-1-chloro-2-(4-trifluoromethoxyphenyl)-5-(3-phenoxy-4-fluorophenyl)penta-2,4-diene as a 2:1 mixture of the (2E, 4E) and (2Z, 4E) isomers.

n-Butyllithium (0.24 cm$^3$ of a 2.5 molar solution in hexane) was added dropwise to a solution of 3-(4-fluoro-3-phenoxyphenyl)prop-2-en-1-yl phosphonate (0.2 g) in dry tetrahydrofuran (5 cm$^3$) at the ambient temperature, under an atmosphere of nitrogen; a deep red colouration was produced. After stirring for 2 hours at the ambient temperature, a solution of 4-trifluoromethoxy-α,α-difluoro-α-chloroacetophenone (0.164 g) in tetrahydrofuran (2 cm$^3$) was added dropwise. Gas liquid chromatography after 30 minutes showed no starting materials present. The mixture was quenched with water and the products extracted into chloroform. The organic layers were dried and concentrated by evaporation under reduced pressure to give a mixture of two isomers of the title compound, confirmed by comparison with an authentic sample of the title compound produced by an alternative route as the (2E, 4E) and (2Z, 4E) isomers in a 2:1 ratio.

EXAMPLE 30

This Example illustrates the preparation of 2-(4-ethoxyphenyl)-5-(3-phenoxyphenyl)-1,1,1-trifluoropentane. A mixture of E and Z isomers of 2-(4-ethoxyphenyl)-3-(3-phenoxyphenyl)-1,1,1-trifluoropent-2-ene (0.4 g) in ethanol (20 cm$^3$) in the presence of a hydrogenation catalyst (10% palladium on charcoal, 50 mg) was stirred under an atmosphere of hydrogen at a pressure of 2 atmospheres for 1 hour, then 4 atmospheres for 4 hours. The reaction mixture was filtered to remove the catalyst and the filtrate concentrated by removal of the ethanol by evaporation under reduced pressure. The residue was dissolved in chloroform, and the solution washed with water twice, dried over anhydrous magnesium sulphate and concentrated by evaporation of the solvent under reduced pressure. The residual oil was purified by column chromatography using a short silica gel column eluted with 2:25 mixture by volume of ethyl acetate and hexane to yield 2-(4-ethoxyphenyl)-3-(3-phenoxyphenyl)-1,1,1-trifluoropentane (0.32 g) as a colourless oil.

$^1$H NMR (CDCl$_3$) δ: 1.42 (t, 3H); 1.5 (m, 2H); 1.9 (m, 2H); 2.55 (m, 2H); 3.16 (m, 1H); 4.03 (q, 2H); 6.75–7.4 (m, 13H).

$^{19}$F NMR (CDCl$_3$) δ: −70.7 (d, 3F).
(relative to CFCl$_3$).

Infra red (liquid film): 1613, 1585, 1515, 1486, 1250, 1218, 1165, 1110 cm$^{-1}$.

EXAMPLE 31

The following compounds were prepared from the appropriate alkene or alkadiene by a procedure similar to that described in Example 30.

(i) 1,1,1-Trifluoro-2-[4-(2-methylprop-2-yl)phenyl]-5-(3-phenoxyphenyl)pentane, from 1,1,1-trifluoro-2-[4-(2-methylprop-2-yl)phenyl]-5-(3-phenoxyphenyl)pent-2-ene.

$^1$H NMR (CDCl$_3$) δ (ppm): 1.34 (9H, s); 1.44–1.60 (2H, m); 1.82–2.1 (2H, m); 2.6 (2H, m); 3.2 (1H, m); 6.8–7.4 (13H, m)

Infra red (liquid film): 1585, 1260, 1110, 695 cm$^{-1}$ 1,1,1-Trifluoro-2-(4-trifluoromethoxyphenyl)-5-(3-phenoxyphenyl)pentane, from 1,1,1-trifluoro-2-(trifluoromethoxyphenyl)-5-(3-phenoxyphenyl)pent-2-ene.

$^1$H NMR (CDCl$_3$) δ (ppm): 1.5 (2H, m); 1.85 (1H, m); 2.0 (1H, m); 2.6 (2H, q); 3.2 (1H, m); 6.75–7.4 (13H, m).

$^{19}$F NMR (CDCl$_3$) δ (ppm—relative to CFCl$_3$) −58.34 (CF$_3$O, s); −70.43 (CF$_3$, d).

(iii) 1,1,1,2,2-Pentafluoro-3-(4-ethoxyphenyl)-6-(3-phenoxyphenyl)hexane from 1,1,1,2,2-pentafluoro-3-(4-ethoxyphenyl)-6-(3-phenoxyphenyl)hex-3-ene.

$^1$H NMR (CDCl$_3$) δ (ppm): 1.4 (3H, t); 1.42 (2H, m) 1.85 (1H, m); 2.0 (1H, m); 2.5–2.6 (2H, m); 3.1–3.2 (1H, dt); 4.0 (2H, q); 6.7–7.4 (13H, m).

Infra red (liquid film): 1615, 1590, 1520, 1490, 1250–1190, 700 cm$^{-1}$ (iv) 1,1,1-Trifluoro-2-(4-trifluoromethylphenyl)-5-(3-phenoxyphenyl)pentane, from 1,1,1-trifluoro-2-(4-trifluoromethylphenyl)-5-(3-phenoxyphenyl)pent-2-ene.

$^1$H NMR (CDCl$_3$) δ (ppm): 1.54 (2H, m); 1.96 (2H, m); 2.56 (2H, m); 3.28 (1H, m); 6.68–7.70 (13H, m).

$^{19}$F NMR (CDCl$_3$) δ (ppm—relative to CFCl$_3$): −63.23 (CF$_3$, s); −70.10 (CF$_3$, d).

(v) 1,1,1-Trifluoro-2-(4-trifluoromethoxyphenyl)-5-(4-fluoro-3-phenoxyphenyl)pentane, from 1,1,1-trifluoro-2-(4-trifluoromethoxyphenyl)-5-(4-fluoro-3-phenoxyphenyl)-pent-2-ene.

$^1$H NMR (CDCl$_3$) δ (ppm): ca 1.5 (2H, m); 1.8, 2.0 (2H, broad m); 2.55 (2H, m); 3.2 (1H, m); 6.7–7.4 (13H, m).

$^{19}$F NMR (CDCl$_3$) δ (ppm—relative to CFCl$_3$): −58.35 (CF$_3$O, s); −70.45 (CF$_3$, d); −135.2 (1F, m).

(vi) 1,1,1-Trifluoro-2-(4-methoxyphenyl)-5-(3-phenoxyphenyl)pentane, from 1,1,1-trifluoro-2-(4-methoxyphenyl)-5-(3-phenoxyphenyl)pent-2-ene $^1$H NMR (CDCl$_3$) δ (ppm): 1.5 (2H, t); 1.8–2.1 (2H, broad m); 2.56 (2H, m); 3.15 (1H, m); 3.8 (3H, s); 6.7–7.4 (13H, m).

(vii) 1,1,1-Trifluoro-2-(4-chlorophenyl)-5-(3-phenoxyphenyl)pentane, from 1,1,1-trifluoro-2-(4-chlorophenyl)-5-(3-phenoxyphenyl)pent-2-ene.

$^1$H NMR (CDCl$_3$) δ (ppm): ca 1.5 (2H, t); 1.8–2.1 (2H, broad m); 2.56 (2H, m); 3.2 (1H, m); 6.75–7.4 (13H, m).

$^{19}$F NMR (CDCl$_3$) δ (ppm—relative to CFCl$_3$): −70.24 (CF$_3$).

(viii) 1,1,1-Trifluoro-2-(4-methoxymethylphenyl)-5-(3-phenoxyphenyl)pentane, from 1,1,1-trifluoro-2-(4-methoxymethylphenyl)-5-(3-phenoxyphenyl)pent-2-ene.

$^1$H NMR (CDCl$_3$) δ (ppm): 1.5 (2H, m); 1.8–2.1 (2H, m); 2.55 (2H, m); 3.23 (1H, m); 3.40 (3H, s); 5.45 (2H, s); 6.75–7.4 (13H, m).

(ix) 1,1,1-Trifluoro-2-(2,4-difluoro-3-trifluoromethoxyphenyl)-5-(3-phenoxyphenyl)-pentane from 1,1,1-trifluoro-2-(2,4-difluoro-3-trifluoromethoxy-6-bromophenyl)-5-(3-phenoxyphenyl)penta-2,4-diene.

NB. Hydrogenation performed at 4.5 atmospheres for 15 hours. The ring bromine was reductively replaced in addition to hydrogenation of the diene.

$^1$H NMR (CDCl$_3$) δ (ppm): 1.5 (2H, m); 1.8, 2.0 (2H, broad m); 2.65 (2H, m); 3.7 (1H, m); 6.7–7.4 (11H, m).

$^{19}$F NMR (CDCl$_3$) δ (ppm—relative to CFCl$_3$): −60.28 (CF$_3$O, t); −70.39 (CF$_3$, dd); −124.47, −128.17 (each 1F, m).

(x) 1,1,1-Trifluoro-2-(3,5-difluoro-4-trifluoromethoxyphenyl)-5-(3-phenoxyphenyl)pentane, from 1,1,1-trifluoro-2-(3,5-difluoro-4-trifluoromethoxyphenyl)penta-2,4-diene.

$^1$H NMR (CDCl$_3$) δ (ppm): 1.5 (2H, m); 1.9, 2.1 (each 1H, m); 2.65 (2H, m); 3.8 (1H, m); 6.8–7.45 (11H, m).

(xi) 1,1,1-Trifluoro-2-(3-fluoro-4-ethoxyphenyl)-5-(3-phenoxyphenyl)pentane, from 1,1,1-trifluoro-2-(3-fluoro-4-ethoxyphenyl)-5-(3-phenoxyphenyl)pent-2-ene.

$^1$H NMR (CDCl$_3$) δ (ppm): 1.44 (3H, t); overlapping with ca 1.5 (2H, m); 1.8, 2.0 (1H, broad m); 2.58 (2H, m); 3.15 (2H, m); 4.1 (2H, q); 6.8–7.4 (12H, m).

(xii) 1,1,1-Trifluoro-2-(3,5-difluoro-4-ethoxyphenyl)-5-(3-phenoxyphenyl)pentane from 1,1,1-trifluoro-2-(3,5-difluoro-4-ethoxyphenyl)-5-(3-phenoxyphenyl)pent-2-ene.

$^1$H NMR (CDCl$_3$) δ (ppm): 1.38 (3H, q); 1.5 (2H, t); ca. 1.76, 1.96 (each 1H, broad m); 2.58 (2H, m); 3.1 (1H, broad m); 4.2 (2H, q); 6.7–7.4 (11H, m).

(xiii) 1,1,1-Trifluoro-2-(3,5-difluoro-4-ethoxyphenyl)-5-(4-fluoro-3-phenoxyphenyl)pentane from 1,1,1-trifluoro-2-(3,5-difluoro-4-ethoxyphenyl)-5-(4-fluoro-3-phenoxyphenyl)penta-2,4-diene.

$^1$H NMR (CDCl$_3$) δ (ppm): 1.4 (3H, t); 1.46 (2H, m); ca 1.76, 1.97 (each 1H, m); 2.55 (2H, m); 3.12 (1H, m); 4.22 (2H, q); 6.7–7.4 (10H, m)

(xiv) 1,1,1-Trifluoro-2-[3,4-(dimethylmethylenedioxy)phenyl]-5-(3-phenoxyphenyl)pentane from 1,1,1-trifluoro-2-[3,4-(dimethylmethylenedioxy)phenyl]-5-(3-phenoxyphenyl)pent-2-ene.

$^1$H NMR (CDCl$_3$) δ (ppm): 1.5 (2H, m); 1.7 (6H, s); ca. 1.8, 1.95 (each 1H, broad m); 2.56 (2H, m); 3.1 (1H, m); 6.6–7.4 (12H, m).

(xv) 1,1,1-Trifluoro-2-[3,4-(methylmethylenedioxy)phenyl]-5-(3-phenoxyphenyl)pentane, from 1,1,1-trifluoro-2-[3,4-(methylmethylenedioxy)phenyl]-5-(3-phenoxyphenyl)pent-2-ene.

$^1$H NMR (CDCl$_3$) δ (ppm): 1.5 (2H, t); ca 1.7 (3H, 2 overlapping doublets due to stereoisomers); 1.8, 2.0 (each 1H, broad m); 2.56 (2H, m); 3.1 (1H, m); 6.25 (1H, 2q); 6.6–7.4 (12H, m).

(xvi) 1,1,1-Trifluoro-2-(4-fluorophenyl)-5-(3-phenoxyphenyl)pentane from 1,1,1-trifluoro-2-(4-fluorophenyl)-5-(3-phenoxyphenyl)pent-2-ene.

$^1$H NMR (CDCl$_3$) δ (ppm): 1.46 (2H, m); 1.8–2.1 (2H, broad m); 2.56 (2H, m); 3.2 (1H, m); 6.7–7.4 (13H, m).

$^{19}$F NMR (CDCl$_3$) δ (ppm—relative to CFCl$_3$): −70.62 (CF$_3$, d); −114.5 (1F, m).

(xvii) 1,1,1-Trifluoro-2-(5-indanyl)-5-(3-phenoxyphenyl)pentane from 1,1,1-trifluoro-2-(5-indanyl)-5-(3-phenoxyphenyl)pent-2-ene.

$^1$H NMR (CDCl$_3$) δ (ppm): ca 1.5 (2H, m); 1.8–2.1 (2H, broad m); overlapping with 2.06 (2H, m); 2.55 (2H, m); 2.88 (4H, t); 3.2 (1H, m); 6.7–7.4 (12H, m).

$^{19}$F NMR (CDCl$_3$) δ (ppm—relative to CFCl$_3$): −70.34 (CF$_3$, d).

(xviii) 1,1,1-Trifluoro-2-(4-ethoxyphenyl)-5-(3-benzyl-4-fluorophenyl)pentane from 1,1,1-trifluoro-2-(4-ethoxyphenyl)-5-(3-benzyl-4-fluorophenyl)penta-2,4-diene.

$^1$H NMR (CDCl$_3$) δ (ppm): 1.4 (5H, t+m); 1.7–2.0 (2H, m); 2.45 (2H, m); 3.1 (1H, m); 3.94 (s, 2H); 4.0 (q, 2H); 6.8–7.3 (12H, m).

(xix) 1,1,1-Trifluoro-2-(4-trifluoromethoxyphenyl)-5-(3-benzyl-4-fluorobenzyl)pentane from 1,1,1-trifluoro-2-(4-trifluoromethoxyphenyl)-5-(3-benzyl-4-fluorobenzyl)penta-2,4-diene.

$^1$H NMR (CDCl$_3$) δ (ppm): 1.4 (2H, m); 1.85 (1H, m); 1.95 (1H, m); 2.45 (2H, m); 3.1 (1H, m); 3.95 (2H, s); 6.8–7.3 (12H, m).

(xx) 1,1-Difluoro-1-chloro-2-(4-ethoxyphenyl)-5-(3-phenoxyphenyl)pentane from 1,1-difluoro-2-chloro-2-(4-ethoxyphenyl)-5-(3-phenoxyphenyl)penta-2,4-diene.

$^1$H NMR (CDCl$_3$) δ (ppm): 1.3–1.6 (5H, m); 1.8–2.1 (2H, m); 2.55 (2H, m); 3.27 (1H, dq); 4.02 (2H, q); 6.7–7.4 (13H, m).

Molecular ion: 430, 432 (two peaks due to chlorine isotypes).

In this case, hydrogenation for 4½ hours at 3.5 atmospheres using a Rhodium on alumina catalyst, produced a complex mixture including partially reduced material. Further hydrogenation (4 hours at 3 atmospheres) of the mixture produced two main components which were separated by high pressure liquid chromatography to give the title product and 1,1-difluoro-2-(4-ethoxyphenyl)-5-(3-phenoxyphenyl)-pentane, identical with the product of Example (xxi) below.

(xxi) 1,1-Difluoro-2-(4-ethoxyphenyl)-5-(3-phenoxyphenyl)pentane from 1,1-difluoro-2-(4-ethoxyphenyl)-5-(3-phenoxyphenyl)penta-2,4-diene.

$^1$H NMR (CDCl$_3$) δ (ppm): 1.41 (3H, t); 1.5 (2H, m); 1.6–1.9 (2H, m); 2.55 (2H, m); 2.9 (1H, m); 4.02 (2H, q); 5.75 (1H, dt J=57 Hz and 5 Hz); 6.7–7.4 (13H, m).

Molecular ion: 396

(xxii) 1,1-Difluoro-2-(4-trifluoromethoxyphenyl)-5-(3-phenoxyphenyl)pentane from 1,1-difluoro-2-(4-trifluoromethoxyphenyl)-5-(3-phenoxyphenyl)penta-2,4-diene.

$^1$H NMR (CDCl$_3$) δ (ppm): 1.6 (2H, m); ca 1.8, 1.95 (each 1H, broad m); 2.6 (2H, m); 3.06 (1H, broad m); 5.84 (1H, dt, J=5 Hz and 54 Hz); 6.8–7.4 (13H, m).

$^{19}$F NMR (CDCl$_3$) δ (ppm—relative to CFCl$_3$): −58.35 (CF$_3$O, s); ca 121.2 (CF$_2$H, dt).

Molecular ion: 436

(xxiii) 1,1,1-Trifluoro-2-(4-ethoxyphenyl)-5-(3-phenoxypyrid-2-yl)pentane from 1,1,1-trifluoro-2-(4-ethoxyphenyl)-5-(3-phenoxypyrid-2-yl)pent-4-ene.

$^1$H NMR (CDCl$_3$) δ (ppm): 1.4 (3H, t); 1.6 (2H, m); 1.8–2.0 (2H, m); 2.6 (2H, m); 3.2 (1H, m); 4.0 (2H, q); 6.6 (1H, m); 6.8–7.6 (11H, m).

(xxiv) 1,1,1-Trifluoro-2-(4-ethoxyphenyl)-5-(pentafluorophenyl)pentane from 1,1,1-trifluoro-2-(4-ethoxyphenyl)-5-(pentafluorophenyl)pent-4-ene.

$^1$H NMR (CDCl$_3$) δ (ppm): 1.4 (3H, t); 1.8–2.0 (2H, m); 2.6 (2H, m); 3.2 (1H, m); 3.7 (2H, m); 4.0 (2H, q); 6.85 (2H, d); 7.2 (2H, d).

(xxv) 1,1,1-Trifluoro-2-(3,4-methylenedioxy)phenyl-5-(3-phenoxyphenyl)pentane from 1,1,1-trifluoro-2-(3,4-methylenedioxyphenyl)-5-(3-phenoxyphenyl)pent-2-ene.

$^1$H NMR (CDCl$_3$) δ (ppm): 1.45 (2H, m); 1.8–2.0 (2H, m); 2.5 (2H, m); 3.15 (1H, m); 6.0 (2H, s); 6.7–7.4 (12H, m).

(xxvi) 1,1,1-Trifluoro-2-(4-ethoxyphenyl)-5-(4-fluoro-3-phenoxyphenyl)pentane from 1,1,1-trifluoro-2-(4-ethoxyphenyl)-5-(4-fluoro-3-phenoxyphenyl)pent-4-ene.

$^1$H NMR (CDCl$_3$) δ (ppm): 1.4 (3H, q); 1.4–1.5 (2H, m); 1.8–2.0 (2H, m); 2.55 (2H, m); 3.15 (1H, m); 4.0 (2H, q); 6.8–7.4 (12H, m).

(xxvii) 1,1,1-Trifluoro-2-(4-ethoxyphenyl)-5-(3-phenoxyphenyl)hexane from 1,1,1-trifluoro-2-(4-ethoxyphenyl)-5-(3-phenoxyphenyl)hex-4-ene. $^1$H NMR (CDCl$_3$) δ (ppm): 1.2 (2H, 2d); 1.4 (3H, 2t) and (2H, m); 1.6 (1H, m); 1.8 (1H, m); 2.6 (1H, m); 3.1 (1H, m); 4.0 (2H, q); 6.8–7.4 (13H, m).

(xxviii) 1,1,1-Trifluoro-2-(4-ethoxyphenyl)-5-cyano-5-(3-phenoxyphenyl)pentane from 1,1,1-trifluoro-2-(4-ethoxyphenyl)-5-cyano-5-(3-phenoxyphenyl)pent-4-ene.

$^1$H NMR (CDCl$_3$) δ (ppm): 1.4 (3H, t) and (1H, m); 1.90–2.15 (1H, m); 2.65 (m, 2H); 3.15 (1H, m); 3.75 (2H, m); 4.0 (2H, q); 6.7–7.4 (13H, m).

(xxix) 1,1-Difluoro-2-(4-trifluoromethoxyphenyl)-5-(4-fluoro-3-phenoxyphenyl)pentane from 1,1-difluoro-1-chloro-2-(4-trifluoromethoxyphenyl)-5-(4-fluoro-3-phenoxyphenyl)penta-2,4-diene.

Hydrogenation of 1,1-difluoro-1-chloro-2-(4-trifluoromethoxyphenyl)-5-(4-fluoro-3-phenoxyphenyl)-penta-2,4-diene at a hydrogen pressure of 4 atmospheres for 5 hours produced a multicomponent mixture of products, two of which were identified as, firstly, the title compound and, secondly, the difluoropent-2-ene of Example 13 (xvii). The products were separated by analytical high pressure liquid chromatography on a 1 inch Dupont silica column eluted with hexane containing 1% by volume ethyl acetate.

Details for title compound (see Example 13 (xvii) for pentene details)

$^1$H NMR (CDCl$_3$) δ (ppm): 1.46 (2H, m); ca 1.7, 1.9 (each 1H, broad m); 2.52 (2H, m); 2.96 (1H, m); 5.77 (1H, dt, J=5 Hz and 56 Hz); 6.8–7.4 (12H, m).

$^{19}$F NMR (CDCl$_3$) δ (ppm—relative to CFCl$_3$): −58.37 (CF$_3$O, s); ca −121.24 (CF$_2$H, m); −135.28 (1F, m).

EXAMPLE 32

This Example illustrates the preparation of 1,1,1-trifluoro-2-(4-hydroxyphenyl)-5-(3-phenoxyphenyl)pentane.

Dry pyridinium hydrochloride (1.57 g) and 1,1,1-trifluoro-2-(4-methoxyphenyl)-5-(3-phenoxyphenyl)-pentane (0.545 g) were mixed and heated at 200° C. for 6 hours. Analysis by gas liquid chromatography indicated no remaining starting material. The mixture was cooled then partitioned between water and chloroform. The aqueous layer was extracted with more chloroform, and the combined organic layers were dried over anhydrous sodium sulphate. The solvents were removed by evaporation under reduced pressure to leave a black oil. Purification by chromatography on silica gel eluting with a 3:1 hexane ethyl acetate mixture gave the title compound (0.47 g).

$^1$H NMR (CDCl$_3$) δ (ppm): 1.47 (2H, t); 1.75–2.05 (2H, m); 2.56 (2H, m); 3.15 (1H, m); 4.7 (1H); 6.7–7.4 (13H, m).

EXAMPLE 33

This example illustrates the preparation of 1,1,1-trifluoro-2-[4-(2-bromo-1,1,2,2-tetrafluoroethoxy)phenyl]-5-(3-phenoxyphenyl)-pentane and 1,1,1-trifluoro-2-[4-(1,1,2,2-tetrafluoroethoxy)phenyl]-5-(3-phenoxyphenyl)pentane.

1,1,1-Trifluoro-2-(4-hydroxyphenyl)-5-(3-phenoxyphenyl)pentane (0.47 g), 1,2-dibromotetrafluoroethane (0.46 g), propane thiol (0.02 g), anhydrous potassium carbonate (0.17 g), dimethylformamide (11 ml) were sealed in a Carius tube and heated at 50° C. for 48 hours. After cooling, the mixture was then poured into 2M sodium hydroxide, and the products were extracted into diethylether. The ether was dried over anhydrous sodium sulphate, and the solvents were removed by evaporation under reduced pressure to leave an orange oil (0.6 g). Chromatography on silica gel eluted with a 19:1 hexane ethylacetate mixture gave a mixture of 2 compounds, identified by gas chromatography—mass spectrometry as the 4-(2-bromo-1,1,2,2-tetrafluoroethoxy)phenyl compound and the 4-(1,1,2,2-tetrafluoroethoxy)phenyl compound in a ratio of about 3:2.

Further elution of the column (with 4:1 hexane/ethylacetate) produced some unchanged phenol.

The mixture of compounds (0.12 g) was heated, under an atmosphere of nitrogen, with tri-n-butyl tin hydride (0.1 cm$^3$), dry toluene (10 cm$^3$) and azobisisobutyronitrile (AIBN, 0.005 g) at the reflux temperature for 4½ hours. The mixture was then concentrated by evaporation under reduced pressure, and the oil obtained was chromatographed on silica gel, eluting with hexane containing 2% by volume ethyl acetate. The residual oil was heated in a Kugelrohr apparatus at 130° C. under reduced pressure (0.1 mmHg) to separate the product from tin residues. The distillate was a colourless oil, (0.094 g) which was found to be 96% pure by gas liquid chromatography, and was identified as 1,1,1-trifluoro-2-[4-(1,1,2,2-tetrafluoroethoxy)phenyl]-5-(3-phenoxyphenyl)-pentane.

$^1$H NMR (CDCl$_3$) δ (ppm): 1.47 (2H, m); 1.8 and 2.0 (each 1H, broad m); 2.56 (2H, m); 3.2 (1H, m); 5.9 (1H, tt J ca 3 Hz and 53 Hz); 6.7–7.4 (13H, m).

$^{19}$F NMR (CDCl$_3$) δ (ppm): −70.4 (CF$_3$, d); −88.7 (CF$_2$O, m); −137.3 (CF$_2$H, dt)

The reaction was repeated using 0.6 g of the starting phenol. The mixture of compounds produced was separated from unreacted phenol (48% by gas liquid chromatographic analysis of the reaction mixture) by chromatography as described above. By further careful chromatography using hexane containing 1% by volume ethyl acetate on silica gel it was possible to obtain the required 1,1,1-trifluoro-2-[4-(1,1,2,2-tetrafluoro-2-bromoethoxy)phenyl]-5-(3-phenoxyphenyl)pentane in pure form.

$^1$H NMR (CDCl$_3$) δ (ppm): 1.47 (2H, m); 1.75–2.1 (2H, broad m); 2.55 (2H, m); 3.2 (1H, m); 6.7–7.35 (13H, m).

$^{19}$F NMR (CDCl$_3$) δ (ppm—relative to CFCl$_3$): −68.6 (CF$_2$Br, t); −70.43 (CF$_3$, d); −86.53 (CF$_2$O, t).

EXAMPLE 34

This Example illustrates the preparation of 1,1,1-trifluoro-2-[4-(2,2,2-trifluoroethoxy)phenyl]-5-(3-phenoxyphenyl)pentane.

A solution of 1,1,1-trifluoro-2-(4-hydroxyphenyl)-5-(3-phenoxyphenyl)pentane (0.5 g) and tetrafluoroboric acid (0.1 cm$^3$) in chloroform was contained in a conical flask fitted with a side arm leading to a trap containing acetic acid. In a second reaction vessel, diazo-2,2,2-trifluoroethane was generated by the dropwise addition of a solution of sodium nitrite (0.99 g) in water (8 cm$^3$) to a cooled solution (0° C.) of 2,2,2-trifluoroethylamine hydrochloride (1.76 g ) in water (8 cm$^3$). The generated diazo compound (a pale yellow gas) was passed into the chloroform solution of the phenol by means of a slow stream of nitrogen passed from the diazo compound generated into the chloroform solution by way of an inlet tube fitted in a rubber bung in the neck of the conical flask. In view of the explosive nature of the diazo compound, no ground glass joints were used in the connected apparatus. This method of diazo compound generation is similar to that described in Anal. Chem. (1982), 54, 529–533.

Following the addition of the diazo compound, both the aqueous and chloroform solutions from the two reaction vessels were cautiously quenched with excess acetic acid. The chloroform solution was washed with water, then with saturated sodium hydrogen carbonate solution, and then dried over anhydrous sodium sulphate. Evaporation of the solvent under reduced pressure gave an oil containing only 3% of the required product (gas liquid chromatographic analysis). Purification by chromatography on silica gel eluting with hexane containing 1% ethyl acetate gave the pure title compound in low overall yield (0.009 g).

$^1$H NMR (CDCl$_3$) δ (ppm): 1.45 (2H, m); ca 1.8, 2.0 (each 1H, broad m); 2.56 (2H, m); 3.16 (1H, broad m); 4.33 (2H, q); 6.7–7.4 (13H, m).

EXAMPLE 35

This Example illustrates the preparation of 1,1,1-trifluoro-2-hydroxy-2-(4-trifluoromethoxyphenyl)-5-(3-phenoxyphenyl)pentane.

A mixture of lithium metal (0.175 g), diethyl ether (10 cm$^3$) and 3-(3-phenoxyphenyl)-1-bromopropane (1.0 g) was sonicated for 35 minutes. A solution of 4-trifluoromethoxy-α,α,α-trifluoroacetophenone (0.9 g) in diethyl ether (2 cm$^3$) was then added. The reaction mixture was quenched in aqueous hydrochloric acid and the products extracted into diethyl ether. The combined organic extracts were dried and concentrated and the residual oil purified by chromatography to give the title compound.

$^1$H NMR (CDCl$_3$) δ (ppm): 1.3 (1H, m); 1.7 (1H, m); 2.0 (1H, m); 2.2 (1H, m); 2.3 (1H, broad s); 2.6 (2H, m); 6.8–7.6 (13H m).

EXAMPLE 36

This Example illustrates the preparation of 1,1,1-trifluoro-2-chloro-2-(4-trifluoromethoxyphenyl)-5-(3-phenoxyphenyl)pentane.

A solution of 1,1,1-trifluoro-2-hydroxy-2-(4-trifluoromethoxyphenyl)-5-(3-phenoxyphenyl)pentane (0.055 g) in acetonitrile (2 cm$^3$) was treated with imidazole (0.05 g) and thionyl chloride (0.05 g) at 0° C. After 2 hours, the reaction mixture was poured into water and the products extracted into diethylether. The combined organic extracts were dried and the solvent evaporated under reduced pressure. The residual oil was purified by chromatography to give the title compound.

$^1$H NMR (CDCl$_3$) δ (ppm): 1.45 (1H, m); 1.9 (1H, m); 2.2–2.8 (4H, m); 6.8–7.6 (13H, m).

EXAMPLE 37

This Example illustrates the preparation of 1,1,1,2-tetrafluoro-2-(4-trifluoromethoxyphenyl)-5-(3-phenoxyphenyl)pentane.

A solution of 1,1,1-trifluoro-2-hydroxy-2-(4-trifluoromethoxyphenyl)-5-(3-phenoxyphenyl)pentane (0.18 g) in dichloromethane (6 cm$^3$) was cooled to −78° C. and diethylaminosulphur trifluoride (0.1 g) was added. The mixture was allowed to warm to room temperature, stirred for a further 20 minutes and poured into water. The products were extracted into dichloromethane. The combined organic extracts were dried and the solvent evaporated under reduced pressure to leave an oil. The oil was purified by chromatography to give 1,1,1,2-tetrafluoro-2-(4-trifluoromethoxyphenyl)-5-(3-phenoxyphenyl)pentane.

$^1$H NMR (CDCl$_3$) δ (ppm): 1.4 (1H, m); 1.7 (1H, m); 2.1–2.3 (2H, m); 2.6 (2H, m); 6.8–7.4 (13H, m).

EXAMPLE 38

This Example illustrates the stages in the preparation of 4-bromo-1,2-(dimethylmethylenedioxy)benzene.
Stage 1: Preparation of 4-bromo-1,2-dihydroxybenzene 1,2-Dihydroxybenzene (48.9 g) was dissolved in dry diethyl ether (350 cm$^3$) and cooled at −30° C. A solution of the complex formed between 1,4-dioxane and bromine (110 g in 500 cm$^3$ diethyl ether—prepared as described in J. Chem. Soc. 3259 (1954) was added, slowly at first, keeping the temperature below −20° C. After the addition was complete, the mixture was poured into excess aqueous sodium metabisulphite solution, which was then extracted with further portions of diethyl ether. The combined organic layers were dried over anhydrous sodium sulphate and evaporated to an oil (68 g) containing 66% of the desired product and 32% of starting material. Separation of these material proved to be difficult and the mixture was therefore treated with additional bromine-dioxane complex (49.6 g) as described above. Following a similar work-up procedure, the residual oil was purified by chromatography on silica gel, eluting with n-hexane containing 33% by volume ethyl acetate, to give 4-bromo-1,2-dihydroxybenzene as a pale brown oil (50 g, 99% pure), which was used immediately in subsequent reactions.
Stage 2: Preparation of 4-bromo-1,2-(dimethylmethylene)dioxy)benzene Phosphorus pentoxide (14.9 g) was added over a period of 10 minutes to a stirred solution of 4-bromo-1,2-dihydroxybenzene (10 g) in dry acetone (200 cm$^3$) maintained at the reflux temperature under an atmosphere of nitrogen.

After 30 minutes a further portion of phosphorus pentoxide (22.4 g) was added and heating continued for a further hour. After cooling, the mixture was poured into water. The solid residue in the flask was washed with acetone which was added to the aqueous mixture. This was extracted several times with diethylether (addition of saturated sodium chloride solution helped the layers to separated). The combined ether layers were washed with 2N sodium hydroxide solution, then washed with water. The yellow solution was dried over sodium sulphate and evaporated to an orange oil. Some decomposition was evident on attempted distillation, the product was instead purified by chromatography on silica gel eluting with n-hexane containing 2% by volume ethyl acetate to give 4-bromo-1,2-(dimethylmethylenedioxy)benzene (1.64 g) as a yellow oil.

$^1$H NMR (CDCl$_3$) δ (ppm): 1.66 (6H, s); 6.57 (1H, m); 6.85 (1H, s) overlapping with 6.9 (1H, s).

EXAMPLE 39

This Example illustrates the preparation of 4-bromo-1,2-(methylmethylenedioxy)benzene.

4-Bromo-1,2-dihydroxybenzene (prepared according to the method of Stage 1 of Example 38 (10 g), vinyl acetate (6.38 g), yellow mercuric oxide (0.53 g), boron trifluoride etherate (0.5 cm$^3$) and dry toluene (50 cm$^3$) were mixed at room temperature and allowed to stir under an atmosphere of nitrogen for 18 hours. The mixture was poured into water and extracted with several portions of diethylether. The combined ether layers were dried over anhydrous sodium sulphate and the solvent evaporated under reduced pressure to leave a black oil (10 g). Chromatography on silica gel eluting with n-hexane containing 5% by volume ethyl acetate gave a clear oil which was heated at 50° C. and 0.1 mmHg to give 4-bromo-1,2-(methylmethylenedioxy)-benzene (4.1 g).

60 MHz $^1$H NMR (CDCl$_3$) δ (ppm): 1.65 (3H, d); 6.25 (1H, q); ca 6.6 (1H, q); 6.87 (1H, s); overlapping with ca. 6.9 (1H, m).

EXAMPLE 40

This Example illustrates the preparation of 4-bromobenzyl methyl ether.

4-Bromobenzyl alcohol (1.87 g) was added over 10 minutes to a stirred suspension of sodium hydride (0.24 g—used directly in the form of 0.48 g of a 50% dispersion in oil) in dry N,N-dimethylformamide (10 cm$^3$) under an atmosphere of nitrogen. Afer evolution of hydrogen had ceased (20 minutes), methyl iodide (1.42 g) was added and the reaction mixture was stirred for a further 10 minutes. The mixture was poured into water and the organic layer separated. The aqueous layer was extracted with diethyl ether. The combined organic layers were dried over anhydrous sodium sulphate, and concentrated by evaporation under reduced pressure. The residual, crude product was purified by column chromatography on a silica gel support, eluting with n-hexane containing 12.5% by volume ethyl acetate, to give 4-bromobenzyl methyl ether (1.6 g).

$^1$H NMR (CDCl$_3$) δ (ppm): 3.44 (3H, s); 4.46 (2H, s); ca. 7.3 (4H, ABq)

EXAMPLE 41

This Example illustrates the stages in the preparation of 4-bromo-2-fluorophenetole.
Stage 1: Preparation of 4-bromo-2-fluorophenol.

A solution of bromine (140.6 g) in carbon disulphide (50 cm$^3$) was added over 3 hours to a stirred solution of 2-fluorophenol (89.68 g) in carbon disulphide (150 cm$^3$), the temperature being maintained at ca. 10° C. throughout the addition by external cooling. The reaction mixture was allowed to stand at the ambient temperature (ca. 20° C.) for 18 hours, and was then poured into an aqueous solution of sodium metabisulphite (100 cm$^3$). The organic layer was separated, washed with aqueous sodium bicarbonate solution (2×100 cm$^3$) and dried over anhydrous sodium sulphate. Removal of the solvent by evaporation under reduced presure gave an oil, which was purified by distillation under reduced pressure to give two fractions, each shown by gas liquid chromatography to contain 97% 4-bromo-2-fluorophenol. Fraction 1 (89.3 g): boiling range 85°–86° C. (ca. 15 mmHg) Fraction 2 (47.5 g): boiling range 86°–87° C. (ca. 15 mmHg)

The fractions were further shown by gas liquid chromatography to contain, respectively, 1% and 1.5% of dibrominated material.

$^1$H NMR (CDCl$_3$) δ (ppm): 5.3 (1H, broad s); 6.9 (1H, t); 7.1–7.3 (2H, m)

Stage 2: Preparation of 4-bromo-2-fluorophenetole.

A mixture of 2-fluoro-4-bromophenol (19.1 g), sodium hydroxide (6 g), ethyl iodide (46.8 g), tetra-n-butylammonium bromide (3.2 g), dichloromethane (250 cm$^3$) and water (250 cm$^3$) was stirred virgorously at the ambient temperature for 5½ hours, then allowed to stand for a further 68 hours. The organic layer was separated and the aqueous layer was washed with dichloromethane; the combined organic layers were dired over anhydrous sodium sulphate. The solvent was removed by evaporation under reduced pressure at a bath temperature maintained below 40° C. The residual oil was purified by column chromatography on a silica gel support, eluting firstly with n-hexane and secondly with dichloromethane. The product-containing fractions were combined, washed with an aqueous solution of sodium metabisulphite, dried over anhydrous sodium sulphate and concentrated by evaporation under reduced pressure to give 4-bromo-2-fluorophenetole (15.2 g) as an oil. The product was shown by gas liquid chromatography to be 93% pure, and was used without further purification.

$^1$H NMR (CDCl$_3$) δ (ppm): 1.45 (3H, t); 4.07 (2H, q); 6.7–7.3 (3H, m)

$^{19}$F NMR (CDCl$_3$) δ (ppm—relative to CFCl$_3$): −131.8 (1F, m)

EXAMPLE 42

This Example illustrates the stages in the preparation of 3-benzyl-4-fluorobenzaldehyde.

Stage 1: Preparation of 3-bromo-4-fluorobenzaldehyde

A solution of 4-fluorobenzaldehyde (49.6 g) in dry dichloromethane (20 cm$^3$) was added to a cooled (0° C.) suspension of powdered aluminium trichloride (90.4 g) in dry dichloromethane (100 cm$^3$). Bromine (70.4 g) was added, and the mixture heated at the reflux temperature for 16 hours. After cooling, the reaction mixture was carefully poured onto ice and extracted with dichloromethane. The combined organic layers were washed with saturated sodium metabisulphite solution, water and brine, then dried over anhydrous magnesium sulphate. Evaporation of the solvent under reduced pressure gave a dark red oil, which was purified by distillation under reduced pressure, using a 10 cm Vigreux column to give 3-bromo-4-fluorobenzaldehyde (45.7 g) as an oil, boiling point 85°–108° C. at 8 mmHg.

Stage 2: Preparation of 2-(3-bromo-4-fluorophenyl)-1,3-dioxolane

A mixture of 3-bromo-4-fluorobenzaldehyde (45.7 g), ethylene glycol (27.93 g), p-toluenesulphonic acid (0.225 g) and dry toluene (110 cm$^3$) was heated at the reflux temperature under a Dean and Stark trap. After 4.5 hours, approximately 12 cm$^3$ of water had collected in the trap, and analysis of the reaction mixture by gas liquid chromatography indicated that no starting aldehyde was present. The mixture was cooled and poured into diethyl ether, washed with saturated sodium bicarbonate solution and brine, and dried over anhydrous magnesium sulphate. Evaporation of the solvent under reduced pressure gave a yellow oil, which was purified by distillation under reduced pressure to give 2-(3-bromo-4-fluorophenyl)-1,3-dioxolane (43.56 g), boiling point 68°–106° C. at 0.004 mmHg.

90 MHz $^1$H NMR (CDCl$_3$) δ (ppm): 4.1 (4H, m); 5.8 (1H, s); 7.0–7.7 (3H, m)

Stage 3: Preparation of 2-(3-benzyl-4-fluorophenyl)-1,3-dioxolane

This compound was prepared by a method analogous to that reported by Minato et al in Tetrahedron Letters, 21, 845, 1980.

Benzyl bromide (2.77 g) was added in one addition to a suspension of activated zinc powder (2.1 g) in dry tetrahydrofuran (20 cm$^3$) under an atmosphere of nitrogen. The reaction mixture was sonicated for 2 hours, allowed to stand for 30 minutes and carefully filtered under an atmosphere of nitrogen. The filtered solution was then added to a mixture of 2-(3-bromo-4-fluorophenyl)-1,3-dioxolane (1 g) and palladium (Pd°) tetratis triphenyl phosphine (0.05 g) in dry tetrahydrofuran (10 cm$^3$) under an atmosphere of nitrogen. The stirred mixture was heated at the reflux temperature for 48 hours, at which time analysis by gas liquid chromatography showed no trace of starting material. The reaction mixture was cooled and poured into diethyl ether. The organic layer was separated, and washed with ammonium chloride solution, water and brine, then dried over anhydrous magnesium sulphate. Evaporation of the solvent under reduced pressure gave a yellow oil which was purified by column chromatography on a silica gel support, using petroleum ether (boiling range 40°–60° C.) containing diethyl ether (progressively inreased from 10% to 20% by volume) as eluent, to give 2-(3-benzyl-4-fluorophenyl)-1,3-dioxolane (0.7 g). The product was used without further purification.

60 MHz $^1$H NMR (CDCl$_3$) δ (ppm): 4.0 (6H, m); 5.7 (1H, s); 6.8–7.5 (8H, m)

Stage 4: Preparation of 3-benzyl-4-fluorobenzaldehyde

A mixture of 2-(3-benzyl-4-fluorophenyl)-1,3-dioxolane (0.7 g) acetone (10 cm$^3$), water (1 cm$^3$) and concentrated sulphuric acid (5 drops) was stirred overnight. The reaction mixture was poured into diethyl ether and the organic layer washed with sodium bicarbonate solution, water and brine, then dried over anhydrous magnesium sulphate. Evaporation of the solvents under reduced pressure gave 3-benzyl-4-fluorobenzaldehyde (0.59 g), which was used without further purification.

$^1$H NMR (CDCl$_3$) δ (ppm): 4.10 (2H, s); 7.20 (6H, m); 7.75 (2H, m); 9.90 (1H, s).

Infra red (liquid film): 1700 cm$^{-1}$.

EXAMPLE 43

This Example illustrates the insecticidal properties of the Products of this invention.

The activity of the Product was determined using a variety of insect pests. The Product was used in the form of liquid preparations containing from 100 to 500 parts per million (ppm) by weight of the Product. The preparations were made by dissolving the Product in acetone and diluting the solutions with water containing 0.1% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

In the case of the species *Musca domestica* (housefly), an additional assessment to determine the knockdown effect of the compounds was performed. Details are given in Table II.

The results of the tests are given in Table III for each of the Products, at the rate in parts per million given in the second column as a grading of mortality designated as A, B or C wherein A indicates 80–100% mortality or knockdown (70–100% for *Meloidogyne incognita*), B indicates 50–79% mortality knockdown or knockdown (50–69% for *Meloidogyne incognita*) and C indicates less than 50% mortality or knockdown.

In Table III the pest organism used is designated by a letter code and the pests species, the support medium or food, and the type and duration of test is given in Table II.

TABLE II

| CODE LETTERS (Table IV) | TEST SPECIES | SUPPORT MEDIUM/FOOD | TYPE OF TEST | DURATION (days) |
|---|---|---|---|---|
| TUa | *Tetranychus urticae* (spider mites - adult) | French bean leaf | Contact | 3 |
| TUe | *Tetranychus urticae* (spider mites - ova) | French bean leaf | Contact | 6 |
| MP | *Myzus persicae* (aphids) | Chinese Cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/maize seed | Residual | 3 |
| BG | *Blattella germanica* (cockroach nymphs) | Plastic pot | Residual | 3 |
| MD | *Musca domestica* (houseflies - adults) | Cotton wool/sugar | Contact | 1 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 3 |
| MI | *Meloidogyne incognita* (Tomato root knot eelworm - larvae) | Semi in-vitro | Residual | 7 |
| CP | *Chilo partellus* (Maize stemborer - larvae) | Oilseed rape | Residual | 3 |

"Contact" test indicates that both pests and medium were treated and "residual" indicates that the medium was treated before infestation with the pests.

TABLE III

| Compound No. | Rate (ppm) | TU$_A$ | TU$_E$ | MP | NL | MD/KD | MD | BG | HV | SP | DB | MI* | CP |
|---|---|---|---|---|---|---|---|---|---|---|---|---|---|
| 1 | 500 | — | — | A | A | A | A | A | A | — | A | B | A |
| 2 | 500 | — | — | A | A | A | A | A | A | — | A | C | A |
| 3 | 500 | B | C | A | C | A | A | A | A | — | A | C | A |
| 4 | 500 | C | C | C | C | C | C | C | A | — | C | C | A |
| 5 | 250 | A | B | A | A | A | A | A | A | — | A | C | A |
| 6 | 250 | C | C | C | C | C | C | A | C | — | C | A | A |
| 7 | 250 | A | A | A | A | C | B | A | A | — | A | C | A |
| 8 | 250 | C | C | C | C | C | C | A | A | — | A | A | A |
| 9 | 250 | A | A | A | A | A | A | A | A | — | A | C | A |
| 10 | 250 | C | C | C | C | C | C | B | C | — | C | C | C |
| 11 | 250 | C | C | C | C | A | C | C | C | — | C | C | C |
| 12 | 500 | C | C | C | A | A | A | A | A | — | A | A | A |
| 15 | 250 | B | C | C | C | C | C | A | A | — | C | C | A |
| 16 | 250 | B | — | A | A | A | A | A | A | — | A | C | A |
| 20 | 100 | B | A | A | A | A | A | A | A | — | A | C | A |
| 26** | 500 | A | — | A | A | A | A | A | A | A | B | — | — |
| 27 | 500 | A | C | A | A | A | A | A | A | A | A | C | — |
| 31 | 250 | C | C | A | A | A | A | A | A | — | A | C | A |
| 32 | 250 | B | C | A | A | A | A | A | A | — | A | C | A |
| 32 | 500 | C | C | C | C | C | C | B | — | — | C | A | — |
| 34 | 250 | C | C | A | C | C | C | C | C | — | C | A | A |
| 35 | 250 | A | C | A | A | A | A | A | A | — | A | C | A |
| 36 | 250 | C | C | A | A | A | A | A | A | — | A | B | A |
| 37 | 250 | C | C | C | C | C | C | B | C | — | C | C | C |
| 38 | 500 | A | C | C | A | B | B | B | — | — | A | — | A |
| 39 | 500 | — | C | C | C | C | C | B | — | — | C | — | A |
| 40 | 500 | C | C | A | C | A | A | B | A | A | A | — | — |
| 41 | 500 | C | C | C | C | A | A | C | B | B | A | — | — |
| 42 | 500 | C | C | C | C | C | C | C | C | C | A | C | — |
| 43 | 500 | C | C | C | C | B | B | B | C | A | A | C | — |
| 44 | 500 | A | C | C | C | C | C | C | C | B | C | C | — |

TABLE III-continued

| Compound No. | Rate (ppm) | TU$_A$ | TU$_E$ | MP | NL | MD/KD | MD | BG | HV | SP | DB | MI* | CP |
|---|---|---|---|---|---|---|---|---|---|---|---|---|---|
| 45 | 500 | C | C | C | A | A | A | C | A | A | A | C | — |
| 46 | 500 | C | C | C | C | C | C | C | A | C | C | C | — |
| 47 | 250 | C | C | C | C | C | C | B | C | B | B | B | — |
| 48 | 250 | C | C | C | C | C | C | B | C | C | B | C | — |
| 49 | 500 | C | C | A | A | A | A | C | A | A | C | C | — |
| 50 | 450 | C | C | A | C | A | A | A | A | A | A | C | — |
| 51 | 500 | C | C | A | C | A | A | A | A | A | A | C | — |
| 52 | 250 | A | C | B | A | C | B | A | A | A | C | C | — |
| 53 | 250 | A | C | A | A | C | A | A | A | A | A | C | — |
| 54 | 500 | C | C | A | A | A | A | C | A | A | C | C | — |
| 55 | 500 | C | C | A | A | A | A | A | A | A | B | C | — |
| 56 | 500 | A | A | A | A | A | A | A | A | A | A | C | — |
| 57 | 500 | A | A | A | A | A | A | A | A | A | A | C | — |
| 58 | 500 | C | A | B | A | A | A | A | C | B | A | C | — |
| 59 | 500 | A | C | C | A | C | C | C | C | C | A | C | — |
| 60 | 250 | A | A | A | A | A | A | A | A | A | A | C | — |
| 61 | 500 | C | C | A | A | A | A | A | A | A | A | C | — |
| 62 | 250 | C | C | C | C | C | C | C | C | C | C | C | — |
| 63 | 500 | A | A | A | A | A | A | A | A | A | A | C | — |
| 64 | 500 | A | A | A | A | A | A | A | A | A | B | C | — |
| 65 | 500 | C | C | C | C | C | C | C | C | C | C | C | — |
| 66 | 500 | C | C | A | A | C | A | A | A | A | A | C | — |
| 67 | 500 | C | C | A | A | C | C | C | A | A | A | C | — |
| 68 | 500 | A | A | C | A | C | A | A | C | B | A | C | — |
| 69 | 500 | C | C | A | A | C | A | A | A | A | A | C | — |
| 70 | 500 | C | C | C | C | C | C | C | C | C | C | B | — |
| 71 | 500 | C | C | A | B | C | C | C | A | A | A | A | — |
| 72 | 500 | B | C | A | B | C | C | A | A | A | A | C | — |
| 73** | 250 | A | — | A | A | A | A | A | A | A | A | — | — |
| 74 | 500 | B | C | C | C | C | C | C | C | C | C | C | — |
| 75 | 500 | C | C | C | C | C | C | C | C | C | C | C | — |
| 76 | 500 | C | C | C | A | C | C | C | C | C | A | C | — |
| 77 | 500 | C | C | A | A | C | C | A | A | A | A | B | — |
| 83 | 500 | A | A | A | A | A | A | A | A | A | A | — | — |
| 98 | 500 | A | C | A | C | A | A | A | A | A | A | — | — |
| 99 | 500 | C | C | B | C | A | A | C | A | B | C | C | — |
| 100 | 500 | C | C | C | B | B | C | C | C | C | C | C | — |
| 105 | 500 | A | A | A | A | C | C | A | C | A | A | — | — |
| 106 | 500 | A | A | A | A | A | A | A | A | A | A | — | — |
| 107 | 500 | C | C | A | B | C | C | C | C | A | A | — | — |
| 108 | 500 | A | A | A | A | A | A | A | A | A | C | — | — |

*Application rate for *Meloidogyne incognita* is half that recorded in the rate column.
**NL result: *Nilaparvata lugens* replaced by *Nephotettix cincticeps* (Green leaf hopper) for tests on these compounds. Methodology as described in Table II for *Nilaparvata lugens*.

We claim:
1. A compound of formula:

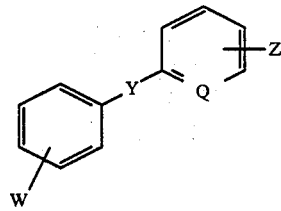

wherein W represents one or more substituents selected from halo, alkyl, alkoxy, alkoxyalkyl, haloalkyl and haloalkoxy or W represents a bidentate group linking adjacent carbon atoms selected from alkylene and alkylenedioxy; Y is a group of formula

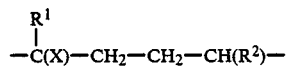

or

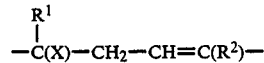

or

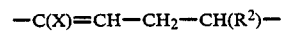

or

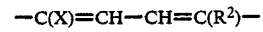

wherein X is a group of formula $-(CF_2)_nR^3$, where $R^3$ is selected from hydrogen, chloro and fluoro, and n is one or two, $R^1$ is selected from hydrogen, chloro, fluoro and hydroxy and $R^2$ is selected from methyl, cyano, ethynyl and hydrogen; Q is selected from carbon bearing a hydrogen atom and nitrogen; and Z represents one or more substituents selected from fluoro, benzyl, phenoxy, chlorophenoxy, fluorophenoxy and bromophenoxy, or any isomer thereof, the alkyl, alkoxy, alkoxyalkyl, haloalkyl and haloalkoxy values for W containing up to six carbon atoms.

2. A compound according to claim 1 having the formula

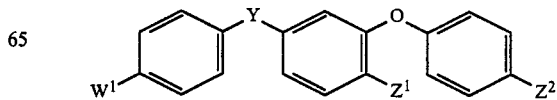

wherein Y is as defined in claim 1; $W^1$ is selected from halo, alkyl of up to six carbon atoms, alkoxy of up to six carbon atoms, haloalkyl of up to six carbon atoms and haloalkoxy of up to six carbon atoms; $Z^1$ is selected from hydrogen and fluoro and $Z^2$ is selected from hydrogen and halo, or any isomer thereof.

3. A compound according to claim 2 having the formula

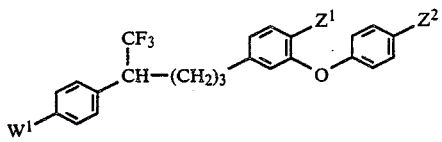

wherein $W^1$ is selected from an alkoxy group of up to two carbon atoms, a fluoroalkoxy group of up to two carbon atoms and a fluoroalkyl group of up to two carbon atoms; $Z^1$ is selected from hydrogen and fluoro and $Z^2$ is selected from hydrogen, bromo, chloro and fluoro, or any isomer thereof.

4. A compound according to claim 1 wherein the group of formula

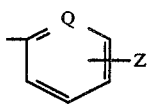

is selected from:
3-phenoxyphenyl,
3-(4-chlorophenonxy)phenyl,
4-fluoro-3-phenoxyphenyl,
3-(4-fluorophenoxy)phenyl,
4-fluoro-3-(4-chlorophenoxy)phenyl,
4-fluoro-3-(4-bromophenoxy)phenyl,
pentafluorophenyl,
6-phenoxypyrid-2-yl,
3-benzylphenyl and
4-fluoro-3-benzylphenyl,
or any isomer thereof.

5. A compound according to claim 1 selected from the group of compounds consisting of:
1,1,1-Trifluoro-2-(4-ethoxyphenyl)-5-(3-phenoxyphenyl)pentane
1,1,1-Trifluoro-2-(4-ethoxyphenyl)-5-(4-fluoro-3-phenoxyphenyl)pentane
1,1,1-Trifluoro-2-(4-trifluoromethoxyphenyl)-5-(3-phenoxyphenyl)pentane
1,1,1-Trifluoro-2-(4-trifluoromethoxyphenyl)-5-(4-fluoro-3-phenoxyphenyl)pentane
1,1-Difluoro-2-(4-ethoxyphenyl)-5-(3-phenoxyphenyl)pentane
1,1-Difluoro-2-(4-trifluoromethoxyphenyl)-5-(3-phenoxyphenyl)pentane
1,1-Difluoro-2-(4-trifluoromethoxyphenyl)-5-(4-fluoro-3-phenoxyphenyl)pentane.

6. An insecticidal composition comprising an insecticidally effective amount of a compound as defined in claim 1 in association with an insecticidally inert diluent or carrier.

7. A method of combating undesirable insects at a locus which comprises applying to the locus an insecticidally effective amount of a composition as defined in claim 6.

8. A compound of formula

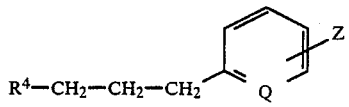

wherein Q and Z have any of the meanings given in claim 1, and $R^4$ is selected from hydroxy, bromo, chloro and iodo, or $R^4$ is selected from a group of formula:

and a group of formula:

wherein R represents alkyl or phenyl.

9. A compound according to claim 8 wherein the group of formula

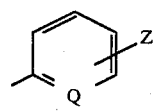

is selected from:
3-phenoxyphenyl,
3-(4-chlorophenoxy)phenyl,
4-fluoro-3-phenoxyphenyl,
3-(4-fluorophenoxy)phenyl,
4-fluoro-3-(4-chlorophenoxy)phenyl,
4-fluoro-3-(4-bromophenoxy)phenyl,
pentafluorophenyl,
6-phenoxypyrid-2-yl,
3-benzylphenyl and
4-fluoro-3-benzylphenyl.

* * * * *